(12) United States Patent
Caracci et al.

(10) Patent No.: US 11,046,931 B2
(45) Date of Patent: *Jun. 29, 2021

(54) SYNTHETIC ATTACHMENT MEDIUM FOR CELL CULTURE

(71) Applicant: Corning Incorporated, Corning, NY (US)

(72) Inventors: Stephen Joseph Caracci, Elmira, NY (US); David Henry, Fontaine le Port (FR); Jessica Jo Kelley, Keene, NY (US); Mark Alan Lewis, Horseheads, NY (US); Yue Zhou, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 37 days.

This patent is subject to a terminal disclaimer.

(21) Appl. No.: 16/371,252

(22) Filed: Apr. 1, 2019

(65) Prior Publication Data

US 2020/0109363 A1    Apr. 9, 2020

Related U.S. Application Data

(63) Continuation of application No. 14/375,614, filed as application No. PCT/US2013/024001 on Jan. 31, 2013, now Pat. No. 10,400,210.

(60) Provisional application No. 61/594,016, filed on Feb. 2, 2012.

(51) Int. Cl.
| | |
|---|---|
| *C12N 5/00* | (2006.01) |
| *C12N 5/0735* | (2010.01) |
| *B65D 3/02* | (2006.01) |
| *C12M 1/00* | (2006.01) |
| *C12N 5/0775* | (2010.01) |
| *B05D 3/02* | (2006.01) |

(52) U.S. Cl.
CPC ......... *C12N 5/0068* (2013.01); *B05D 3/0254* (2013.01); *C12M 23/20* (2013.01); *C12N 5/0037* (2013.01); *C12N 5/0056* (2013.01); *C12N 5/0606* (2013.01); *C12N 5/0663* (2013.01); *C12N 2500/90* (2013.01); *C12N 2500/98* (2013.01); *C12N 2533/30* (2013.01); *C12N 2533/40* (2013.01); *C12N 2533/50* (2013.01)

(58) Field of Classification Search
None
See application file for complete search history.

(56) References Cited

U.S. PATENT DOCUMENTS

| | | |
|---|---|---|
| 5,498,407 A | 3/1996 | Atlas |
| 5,643,561 A | 7/1997 | Katsuen et al. |
| 6,150,459 A | 11/2000 | Mayes et al. |
| 8,530,236 B2 | 9/2013 | Fadeev et al. |
| 2007/0190036 A1 | 8/2007 | Kizilel et al. |
| 2009/0191632 A1* | 7/2009 | Fadeev ............... C12N 5/0606 435/395 |
| 2011/0275154 A1 | 11/2011 | Martin et al. |
| 2015/0010999 A1 | 1/2015 | Caracci et al. |

FOREIGN PATENT DOCUMENTS

| | | |
|---|---|---|
| NO | 1989005150 | 6/1989 |
| NO | 2011014605 A1 | 2/2011 |
| WO | 2010138687 A1 | 12/2010 |
| WO | WO-2011014605 A1 * | 2/2011 ........... C12N 5/0068 |

OTHER PUBLICATIONS

Harris (*S. aureus* adhesion to titanium oxide surfaces coated with non-functionalized and peptide-functionalized poly(l-lysine)-grafted-poly(ethylene glycol) copolymers, 2004) (Year: 2004).*
Besse and Moroder, "Synthesis of Selenocysteine peptides and their oxidation to diselenide-bridged compounds" 1997, Journal of Peptide Science, vol. 3, 442-453.
Braam et al. "Recombinant vitronectin is a functionally defined substrate that supports human embryonic stem cell self-renewal via alphavbeta5 integrin" Stem Cells (2009) 26(9) pp. 2257-2265.
Burgener A, Butler. "Medium Development". In Cell Culture Technology for Pharmaceutical and Cell-Based Therapies. Edited by Ozturk SS and Hu WS. 2006.
IN6486/DELNP/2014 First Examination Report dated Feb. 26, 2019, India Patent Office.
Kitajima et al. "Clonal expansion of human pluripotent stem cells on gelatin-coated surface" Biochemical and Biophysical Research Communications (2010) 396(4) pp. 933-938.
Koide et al, "Synthetic study on selenocystine-containing peptides" 1993, Chem. Pharm. Bull. 41(3):502-506.
Koide et al.,1993, "Syntheses and biological activities of selenium analogs of -Rat Atrial" Chem. Pharm. Bull. 41(9):1596-1600.
Konkolewicz et al. "Dendritic and hyperbranched polymers from macromolecular units: elegant approaches to the synthesis of functional polymers" 2011 American Chemical Society Publications, Macromolecules vol. 44, pp. 7067-7087.
Mallon BS et al. "Toward xeno-free culture of human embryonic stem cells" The International Journal of Biochemistry & Cell Biology 38, p. 1063-1075 (2006.

(Continued)

*Primary Examiner* — Nghi V Nguyen
(74) *Attorney, Agent, or Firm* — Annie J. Kock

(57) ABSTRACT

An aqueous cell culture medium composition includes an aqueous cell culture solution configured to support the culture of mammalian cells. The composition further includes a synthetic polymer conjugated to a polypeptide dissolved in the aqueous cell culture solution. The synthetic polymer conjugated to a polypeptide is configured to attach to the surface of a cell culture article under cell culture conditions. Incubation of the aqueous cell culture medium composition on a cell culture surface under cell culture conditions results is attachment to the surface of the synthetic polymer conjugated to the polypeptide.

17 Claims, 8 Drawing Sheets
Specification includes a Sequence Listing.

(56) References Cited

OTHER PUBLICATIONS

Melkournian et al. "Synthetic peptide-acrylate surfaces for long-term self-renewal and cardiomyocyte differentiation of human embryonic stem cells" Nature Biotechnology (2010) 28(6) pp. 606-610.
Rodin S et al. "Long-term self-renewal of human pluripotent stem cells on human recombinant laminin-511" nature Biotechnology 28, p. 611-615 (2010.
Tekkatte et al. "Review Article: "Humanized" Stem Cell Culture Techniques: The Animal Serum Controversy" Stem Cells International, vol. 2011 Article ID 504723, 14 pgs.
Villa-Diaz et al "Concise Review: the evolution of huan pluripotent stem cell culture: from feeder cells to synthetic coatings" Stem Cells (2013) 31(1) pp. 1-7.
Villa-Diaz LG et al. "Synthetic polymer coatings for long term growth of human embryonic stem cells" Nature Biotechnology 28, p. 581-583 (2010.
Bo (Brain Heart Infusion (BHI) Agar).
CN201380016144.X First Office Action dated Nov. 26, 2015, China Patent Office.
Harris (*S. aureus* adhesion to titanium oxide surfaces coated with non-functionalized and peptide-functionalized poly(l-lysine)-grafted-poly(ethylene glycol) copolymers, 2004).
Akopian V et al. "Comparison of defined culture systems for feeder cell free propagation of human embryonic stem cells" In Vitro Cellular Developmental Biology Animal 46(3-40, p. 247-258 (2010.

\* cited by examiner

SEQUENCE LISTING

```
<160> NUMBER OF SEQ ID NOS: 33

<210> SEQ ID NO 1
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 1

Lys Gly Gly Gly Gln Lys Cys Ile Val Gln Thr Thr Ser Trp Ser Gln
1               5                   10                  15

Cys Ser Lys Ser
            20

<210> SEQ ID NO 2
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 2

Gly Gly Gly Gln Lys Cys Ile Val Gln Thr Thr Ser Trp Ser Gln Cys
1               5                   10                  15

Ser Lys Ser

<210> SEQ ID NO 3
<211> LENGTH: 13
<212> TYPE: PRT
<213> ORGANISM: Artificial Sequence
<220> FEATURE:
```

<223> OTHER INFORMATION: Synthetic polypeptide

<400> SEQUENCE: 3

Lys Tyr Gly Leu Ala Leu Glu Arg Lys Asp His Ser Gly
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 4

Tyr Gly Leu Ala Leu Glu Arg Lys Asp His Ser Gly
1               5                   10

<210> SEQ ID NO 5
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 5

Lys Gly Gly Ser Ile Asn Asn Asn Arg Trp His Ser Ile Tyr Ile Thr
1               5                   10                  15

Arg Phe Gly Asn Met Gly Ser
            20

<210> SEQ ID NO 6
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 6

Gly Gly Ser Ile Asn Asn Asn Arg Trp His Ser Ile Tyr Ile Thr Arg
1               5                   10                  15

Phe Gly Asn Met Gly Ser
            20

<210> SEQ ID NO 7
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 7

Lys Gly Gly Thr Trp Tyr Lys Ile Ala Phe Gln Arg Asn Arg Lys
1               5                   10                  15

<210> SEQ ID NO 8
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 8

Gly Gly Thr Trp Tyr Lys Ile Ala Phe Gln Arg Asn Arg Lys
1               5                   10

```
<210> SEQ ID NO 9
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 9

Lys Gly Gly Thr Ser Ile Lys Ile Arg Gly Thr Tyr Ser Glu Arg
1               5                   10                  15

<210> SEQ ID NO 10
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 10

Gly Gly Thr Ser Ile Lys Ile Arg Gly Thr Tyr Ser Glu Arg
1               5                   10

<210> SEQ ID NO 11
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 11

Lys Tyr Gly Thr Asp Ile Arg Val Thr Leu Asn Arg Leu Asn Thr Phe
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 12

Tyr Gly Thr Asp Ile Arg Val Thr Leu Asn Arg Leu Asn Thr Phe
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 13

Lys Tyr Gly Ser Glu Thr Thr Val Lys Tyr Ile Phe Arg Leu His Glu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 14

Tyr Gly Ser Glu Thr Thr Val Lys Tyr Ile Phe Arg Leu His Glu
1               5                   10                  15

<210> SEQ ID NO 15
```

```
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 15

Lys Tyr Gly Lys Ala Phe Asp Ile Thr Tyr Val Arg Leu Lys Phe
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 16

Tyr Gly Lys Ala Phe Asp Ile Thr Tyr Val Arg Leu Lys Phe
1               5                   10

<210> SEQ ID NO 17
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 17

Lys Tyr Gly Ala Ala Ser Ile Lys Val Ala Val Ser Ala Asp Arg
1               5                   10                  15

<210> SEQ ID NO 18
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 18

Tyr Gly Ala Ala Ser Ile Lys Val Ala Val Ser Ala Asp Arg
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 19

Cys Gly Gly Asn Gly Glu Pro Arg Gly Asp Thr Tyr Arg Ala Tyr
1               5                   10                  15

<210> SEQ ID NO 20
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 20

Gly Gly Asn Gly Glu Pro Arg Gly Asp Thr Tyr Arg Ala Tyr
1               5                   10

<210> SEQ ID NO 21
<211> LENGTH: 14
```

```
<212> TYPE: PRT
<213> ORGANISM: Artificial Sequence
<220> FEATURE:
<223> OTHER INFORMATION: Synthetic polypeptide

<400> SEQUENCE: 21

Cys Gly Gly Asn Gly Glu Pro Arg Gly Asp Thr Arg Ala Tyr
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 22

Gly Gly Asn Gly Glu Pro Arg Gly Asp Thr Arg Ala Tyr
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 23

Lys Tyr Gly Arg Lys Arg Leu Gln Val Gln Leu Ser Ile Arg Thr
1               5                   10                  15

<210> SEQ ID NO 24
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 24

Tyr Gly Arg Lys Arg Leu Gln Val Gln Leu Ser Ile Arg Thr
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 25

Lys Gly Gly Arg Asn Ile Ala Glu Ile Ile Lys Asp Ile
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 26

Gly Gly Arg Asn Ile Ala Glu Ile Ile Lys Asp Ile
1               5                   10

<210> SEQ ID NO 27
<211> LENGTH: 15
<212> TYPE: PRT
```

<213> ORGANISM: Artificial Sequence
<220> FEATURE:
<223> OTHER INFORMATION: Synthetic polypeptide

<400> SEQUENCE: 27

Lys Gly Gly Pro Gln Val Thr Arg Gly Asp Val Phe Thr Met Pro
1               5                   10                  15

<210> SEQ ID NO 28
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 28

Gly Gly Pro Gln Val Thr Arg Gly Asp Val Phe Thr Met Pro
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 29

Gly Arg Gly Asp Ser Pro Lys
1               5

<210> SEQ ID NO 30
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 30

Lys Gly Gly Ala Val Thr Gly Arg Gly Asp Ser Pro Ala Ser Ser
1               5                   10                  15

<210> SEQ ID NO 31
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 31

Gly Gly Ala Val Thr Gly Arg Gly Asp Ser Pro Ala Ser Ser
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic polypeptide
<220> FEATURE:
<221> NAME/KEY: Xaa
<222> LOCATION: (1)..(1)
<223> OTHER INFORMATION: Xaa = any amino acid

<400> SEQUENCE: 32

Xaa Pro Gln Val Thr Arg Gly Asp Val Phe Thr Met Pro
1               5                   10

```
<210> SEQ ID NO 33
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 33

Arg Gly Asp Tyr Lys
1               5
```

SYNTHETIC ATTACHMENT MEDIUM FOR CELL CULTURE

CROSS-REFERENCE TO RELATED APPLICATIONS

This application is a continuation application and claims the benefit of priority under 35 U.S.C. § 120 to U.S. patent application Ser. No. 14/375,614 filed on Jul. 30, 2014, which claims the benefit of priority to International Application No. PCT/US13/24001 filed on Jan. 31, 2013, which claims the benefit of priority under 35 U.S.C. § 119 of U.S. Provisional Application Ser. No. 61/594,016 filed on Feb. 2, 2012 the content of which each is relied upon and incorporated herein by reference in their entirety.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Mar. 25, 2013, is named "20130325_SP12-014_PCT_SEQUENCE_LISTING_ST25" and is 8 KB bytes in size.

FIELD

The present disclosure relates to cell culture, and more particularly to media for cell culture containing synthetic, chemically-defined polymers and methods for cell culture and for coating substrates using such media.

BACKGROUND

Therapeutic cells, cells which may be introduced into a human for the treatment of disease, are being developed. Examples of therapeutic cells include stem cells such as human embryonic stem cells (hESCs) and human mesenchymal stem cells (hMSCs). which have the ability to differentiate to various cell types in the human body. This property of stem cells provides a potential for developing new treatments for a number of serious cell degenerative diseases, such as diabetes, spinal cord injury, heart diseases and the like. However, there remain obstacles in the development of such cell-based treatments.

Obtaining and maintaining adequate numbers of therapeutic cells in cell and tissue culture and ensuring that these cells do not change in unwanted ways during cell culture are important in developing and controlling therapeutic cell cultures. For example, stem cell cultures are typically seeded with a small number of cells from a cell bank or stock and then amplified in the undifferentiated or partially differentiated state until differentiation is desired for a given therapeutic application. To accomplish this, the stem cell or their differentiated cells are typically cultured in the presence of surfaces or media containing animal-derived components, such as feeder layers, serum, or Matrigel™ available from BD Biosciences, Franklin Lakes N.J. These animal-derived additions to the culture environment may expose the cells to potentially harmful viruses or other infectious agents which could be transferred to patients or which could compromise general culture and maintenance of the hESCs. In addition, such biological products are vulnerable to batch variation, immune response and limited shelf-life.

Recently, synthetic surfaces that are free of animal-derived components have been shown to be successful in the culture of stem cells in chemically defined medium, addressing many of the issues that result from culturing cells in the presence of animal-derived components. However, such synthetic surfaces have been made with high concentrations of recombinant polypeptides, which can be expensive to manufacture. In some cases, synthetic surfaces require the use organic solvents for purposes of coating, as water soluble coating materials often cannot adequately remain bound to a surface under cell culture conditions.

BRIEF SUMMARY

Among other things, the present disclosure describes peptide-polymers capable of supporting growth and attachment of stem cells in chemically defined medium, where the peptide-polymers may be added to cell culture medium as a supplement to enhance cell attachment to uncoated surfaces. The peptide polymers have been found to form stable coatings on cell culture substrate surfaces when introduced as a supplement to cell culture media.

In various embodiments described herein, an aqueous cell culture medium composition comprises (i) an aqueous cell culture solution configured to support the culture of mammalian cells; and (ii) a synthetic polymer conjugated to a polypeptide dissolved in the aqueous cell culture solution, wherein the synthetic polymer conjugated to a polypeptide is configured to attach to the surface of a cell culture article under cell culture conditions, and wherein incubation of the aqueous cell culture medium composition on a cell culture surface under cell culture conditions results in attachment to the surface of the synthetic polymer conjugated to the polypeptide. The cell culture medium may be a chemically defined composition or may be substantially free of organic solvents. In embodiments, the polymer has a linear backbone and is crosslink free, wherein the synthetic polymer conjugated to the polypeptide is soluble in water at 20° C. or less. In embodiments, the cell culture medium comprises glucose and one or more amino acids.

In embodiments, a method described herein comprises (i) introducing a synthetic polymer having a covalently attached polypeptide to an aqueous cell culture medium to produce a polymer containing cell culture medium, wherein the synthetic polymer conjugated to a polypeptide is configured to attach to the surface of a cell culture article under cell culture conditions; (ii) disposing the polymer containing cell culture medium on the surface of the cell culture article to produce a coated article; and (iii) incubating the coated article in the medium under cell culture conditions (e.g., at 37° C.) to attach the synthetic polymer conjugated to the polypeptide to the surface of the cell culture article. The surface of the substrate may have a water contact angle between 0° and 50°. In embodiments, the surface of the substrate is a plasma treated polystyrene surface. The method may further include incubating cells (such as stem cells; e.g., human mesenchymal stem cells or human embryonic stem cells) on the coated article in the medium under cell culture conditions. The method may further comprise introducing cells into the polymer containing cell culture medium prior to contacting the polymer containing cell culture medium to the surface of the cell culture article.

One or more embodiments of the cell culture articles, compositions, or methods described herein provide one or more advantages over prior cell culture articles, compositions, or methods for producing coated cell culture articles. For example, because the coating is fully synthetic, it does not suffer from batch variation, immune response, limited shelf-life and risk of exposure of the cells to potentially harmful viruses or other infectious agents which could be transferred to patients. In various embodiments, the coating is formed in situ from a peptide polymer present in a cell culture medium under typical cell culture conditions. These and other advantages will be readily understood from the following detailed description when read in conjunction with the accompanying drawings.

BRIEF DESCRIPTION OF THE DRAWINGS

FIG. 5a on TCT surface precoated with MesenCult-XF Attachment Substrate (MC-ASB); FIG. 5b on TCT surface in medium supplemented with 0.037 mg/ml MC-ASB; FIG. 5c on TCT surface in medium supplemented with 0.0074 mg/ml MC-ASB.

FIG. 6a on polyHEMA-co-VN pre-coated CellBind® surface; FIG. 6b on CellBind® surface without attachment supplement; FIG. 6c on CellBind® surface in media supplemented with 0.006 mg/ml poly-HEMA-co-VN; FIG. 6d on CellBind® surface in media supplemented with 0.012 mg/ml polyHEMA-co-VN; FIG. 6e on CellBind® surface in media supplemented with 0.025 mg/ml polyHEMA-co-VN; FIG. 6f on CellBind® surface in media supplemented with 0.050 mg/ml polyHEMA-co-VN.

FIG. 7a on TCT surface precoated with MC-ASB; FIG. 7b on TCT surface in medium supplemented with 0.037 mg/ml MC-ASB; FIG. 7c on TCT surface in medium supplemented with 0.0074 mg/ml MC-ASB; FIG. 7d on polyHEMA-co-VN pre-coated CellBind® surface; FIG. 7e on CellBind® surface without supplement; FIG. 7f on CellBind® surface in media supplemented with 0.006 mg/ml polyHEMA-co-VN; FIG. 7g on CellBind® surface in media supplemented with 0.012 mg/ml polyHEMA-co-VN; FIG. 7h on CellBind® surface in media supplemented with 0.025 mg/ml polyHEMA-co-VN; FIG. 7i on CellBind® surface in media supplemented with 0.050 mg/ml polyHEMA-co-VN.

FIG. 10a on CellBind® surface in media supplemented with 0.025 mg/ml polyHEMA-co-VN; FIG. 10b on CellBind® surface in media supplemented with 0.006 mg/ml polyHEMA-co-VN; FIG. 10c on Matrigel® coated control surface.

FIG. 11a on CellBind® surface in media supplemented with 0.025 mg/ml poly-HEMA-co-VN; FIG. 11b on CellBind® surface in media supplemented with 0.006 mg/ml polyHEMA-co-VN; FIG. 11c on Matrigel® coated control surface.

Figure 1:
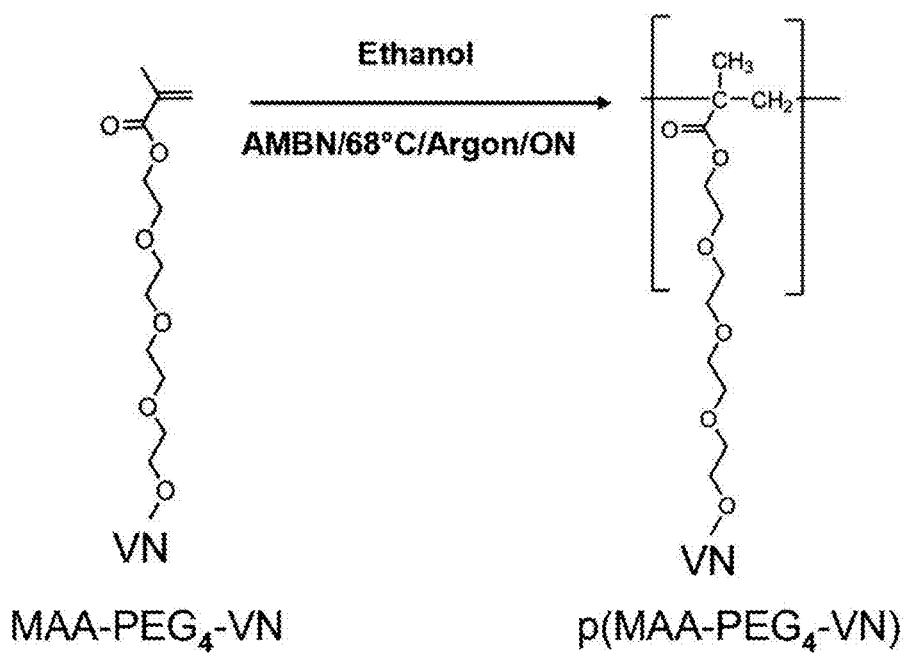
FIG. 1 is a reaction scheme for making a poly(MAA-PEG4-VN) homopolymer having a conjugated cell adhesive polypeptide.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like.

As used herein, "conjugated," as it relates to a monomer or polymer and a polypeptide, means that the polypeptide is covalently bound, either directly or indirectly (e.g., via a spacer) to the polymer or monomer.

As used herein, "monomer" means a compound capable of polymerizing with another monomer, (regardless of whether the "monomer" is of the same or different compound than the other monomer).

As used herein, a "(meth)acrylate monomer" means a methacrylate monomer or an acrylate monomer. As used herein "(meth)acrylamide monomer" means a methacrylamide or an acrylamide monomer. (Meth)acrylate and (meth) acrylamide monomers have at least one ethylenically unsaturated moiety. "Poly(meth)acrylate", as used herein, means a polymer formed from one or more monomers including at least one (meth)acrylate monomer. "Poly(meth)

acrylamide", as used herein, means a polymer formed from one or more monomers including at least one (meth)acrylamide monomer.

As used herein, a polymer without conjugated polypeptide that is "substantially similar" to a polymer conjugated to the polypeptide is a polymer that formed in the same manner as the polymer conjugated to the polymer conjugated to the polypeptide except that the polypeptide is not included. For example, a polypeptide may be conjugated to a polymer via grafting after the polymer is formed. In such cases, the substantially similar polymer that is not conjugated to the polypeptide is the polymer that has not been grafted. By way of further example, a monomer may be derivatized with a polypeptide and the polypeptide may be incorporated into the polymer as the monomer is polymerized or copolymerized. In such cases, the substantially similar polymer that is not conjugated to the polypeptide is a polymer formed under the same reaction conditions as the polymer conjugated to the polypeptide except that the monomer is not derivatized with the polypeptide.

Polypeptide sequences are referred to herein by their one letter amino acid codes or by their three letter amino acid codes. These codes may be used interchangeably.

As used herein, "peptide" and "polypeptide" mean a sequence of amino acids that may be chemically synthesized or may be recombinantly derived, but that are not isolated as entire proteins from animal sources. For the purposes of this disclosure, peptides and polypeptides are not whole proteins. Peptides and polypeptides may include amino acid sequences that are fragments of proteins. For example peptides and polypeptides may include sequences known as cell adhesion sequences such as RGD. Polypeptides may be of any suitable length, such as between three and 30 amino acids in length. Polypeptides may be acetylated (e.g. Ac-LysGlyGly) or amidated (e.g.SerLysSer-$NH_2$) to protect them from being broken down by, for example, exopeptidases. It will be understood that these modifications are contemplated when a sequence is disclosed.

As used herein, "chemically-defined medium" means cell culture media that contains no components of unknown composition. Chemically defined media may, in various embodiments, contain no proteins or hydrosylates.

In embodiments, the polymers and polypeptides described herein are "synthetic." That is, they do not contain ingredients that are derived from animals or animal extracts. Polymers or monomers may be conjugated to polypeptides ("polymer-polypeptide" or "monomer-polypeptide"). Polypeptides may be synthesized or obtained through recombinant techniques, making them synthetic, non-animal-derived materials.

The present disclosure describes, among other things, compositions and methods for culturing cells or for coating cell culture articles. The compositions and methods include a synthetic polymer having a conjugated polypeptide. The synthetic polymer-peptide is water soluble, but attaches to a surface of a cell culture article under typical mammalian cell culture conditions, such as incubation in the medium at about 37° C. It will be understood that cell culture conditions do not include exposure to radiation, such as UV radiation, at levels above background or ambient levels.

The polymer-peptide may be added to, or may be a part of, cell culture medium as an attachment supplement. Cells may be added to cell culture medium containing the polymer-peptide, and the cell-seeded medium may be disposed on, or contacted with, a cell culture article. Under cell culture conditions, e.g. incubation in the medium at about 37° C., the polymer-peptide attaches to the surface of the cell culture article, and the cells attach to the peptide of the polymer peptide. Thus, the cells attach to the surface of the cell culture article via the polymer-peptide.

In embodiments described herein, cell attachment to the surface of the cell culture article is enhanced by adding the polymer-peptide to the medium and contacting to an uncoated cell culture article, relative to contacting cells in medium without the polymer-peptide to an article that has been pre-coated with the polymer-peptide.

Synthetic Polymer-Peptide

Any suitable water-soluble polymer having a conjugated polypeptide may be employed as a cell culture medium attachment supplement, provided that the polymer attaches to a surface of a cell culture article when incubated in the medium under typical cell culture conditions. In embodiments, the synthetic polymers and conjugated polypeptides described herein are soluble in cold (e.g., less than 20° C.) or room temperature (25° C.) water but become securely attached to a substrate when exposed to typical cell culture conditions (e.g., about 37° C.). In embodiments, the synthetic polymers and conjugated polypeptides become securely attached to a substrate at temperatures around room temperature (e.g., at about 25° C.). The synthetic polymers and conjugated polypeptides may be modified to provide for substrate attachment at any desired temperature. In embodiments, the polymers are free of crosslinkers or cross-link free, yet they attach to a cell culture substrate when contacted with the substrate in an aqueous medium, such as cell culture medium. Attachment of the polymer-polypeptide to the substrate occurs without subjecting to levels of radiation, e.g. UV radiation, above typical background levels of radiation.

The polymers conjugated to polypeptide described herein may be water soluble at room temperature or below. However, in embodiments, a substantially similar polymer that is not conjugated to the polypeptide is not water soluble at room temperature or below. In such embodiments, the polypeptide serves to render the polymers conjugated to polypeptide water soluble. In embodiments, the substantially similar polymer that is not conjugated to the polypeptide is not water soluble at cell culture temperatures, which is typically 37° C. but may be lower, such as room temperature (25° C.). It may also be desirable for the polymer to be swellable in water at 37° C. or a desired temperature for cell culture, to provide a suitable modulus for cell culture.

The polymers conjugated to the polypeptides may be formed by any suitable process using any suitable monomers. In embodiments, the one or more monomers used to form the polymer and the reaction mechanisms (e.g., step-growth polymerization or condensation polymerization, or chain polymerization or addition polymerization) used to form the polymer are selected to form polymers with linear polymer backbones. In embodiments, the one or more monomers used to form the polymer and the reaction mechanisms used to form the polymer are selected to form polymers with branched polymer backbones. The branched polymers may be free of cross links. In embodiments, the one or more monomers used to form the polymer and the reaction mechanisms used to form the polymer are selected to form star. To form branched or star polymers multifunctional monomers may be employed in combination with monofunctional monomers. Suitable reaction schemes for forming branched or dendritic or star polymers are discussed in, for example, Konkolewicz, et al., Dendritic and hyperbranched polymers from macromolecular units: Elegant Approaches to the Synthesis of Functional Polymers, Macromolecules, 2011, 44:7067-7087. Of course any other suitable techniques may be employed.

In many embodiments, the monomers used to form the polymers contain an ethylenically unsaturated group, such as (meth)acrylates, (meth)acrylamides, maleimides, fumurates, vinylsulfones, or the like. The polymers may be homopolymers or copolymers. The monomers may be chosen such that the polymer is insoluble or less soluble in water at 37° C., 25° C., etc., but is soluble in water in the range of 4° C. to 25° C., 4° C. to 15° C. or 20° C., etc., when conjugated to the polypeptide.

In various embodiments, a monomer employed is a (meth)acrylate monomer of Formula (I):

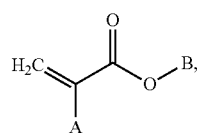

where A is H or methyl, and where B is H, C1-C6 straight or branched chain alcohol or ether, or C1-C6 straight or branched chain alkyl substituted with a carboxyl group (—COOH). In some embodiments, B is C1-C4 straight or branched chain alcohol. In some embodiments, B is straight or branched chain C1-C3 substituted with a carboxyl group. By way of example, 2-carboxyethyl methacrylate, 2-carboxyethyl acrylate, acrylic acid, methacrylic acid, hydroxypropyl methacrylate, 2-hydroxyethyl methacrylate, 2-hydroxyethyl acrylate, glycerol methacrylate, hydroxypropyl acrylate, 4-hydroxybutyl acrylate, or the like may be employed.

In various embodiments, a monomer employed is a (meth)acrylamide monomer of Formula (II):

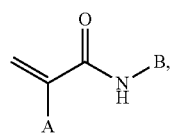

where A is hydrogen or methyl, and where B is H, C1-C6 straight or branched chain alcohol or ether, or C1-C6 straight or branched chain alkyl substituted with a carboxyl group (—COOH). In some embodiments, B is straight or branched chain C1-C3 substituted with a carboxyl group. In some embodiments, B is C1-C4 straight or branched chain alcohol. By way of example, 2-carboxyethyl acrylamide, acrylamidoglycolic acid, N-(hydroxymethyl)acrylamide, N-[Tris(hydroxymethyl)methyl]acrylamide, 3-acryloylamino-1-propanol, N-acrylamido-ethoxyethanol, N-hydroxyethyl acrylamide, or the like, may be used.

The monomer or monomers used to form the polymer may be selected to achieve a polymer having the desired characteristics (e.g., modulus, swellability, water solubility). For example, copolymers formed from more than one monomer may have a greater degree of swellability than homopolymers formed from any one of the monomers alone. Generally, monomers having longer chain alkyl groups will tend to render the polymer too water insoluble for the conjugated polypeptide to make the polymer-polypeptide water soluble at appropriate temperatures. Additionally, monomers having moieties that favor hydrogen bonding or that are charged at selected pH levels may tend to make the polymer more water soluble. One of skill in the art will readily be able to select the appropriate monomers and monomer ratios for preparing polymers having desired characteristics.

Once the appropriate monomers in the appropriate amounts are selected, the polymer may be formed via polymerization reaction. In addition to the monomers that form the polymer, a composition may include one or more additional compounds such as surfactants, wetting agents, photoinitiators, thermal initiators, catalysts, and activators.

Any suitable polymerization initiator may be employed. One of skill in the art will readily be able to select a suitable initiator, e.g. a radical initiator or a cationic initiator, suitable for use with the monomers. In various embodiments, UV light is used to generate free radical monomers to initiate chain polymerization. Examples of polymerization initiators include organic peroxides, azo compounds, quinones, nitroso compounds, acyl halides, hydrazones, mercapto compounds, pyrylium compounds, imidazoles, chlorotriazines, benzoin, benzoin alkyl ethers, diketones, phenones, or mixtures thereof. Examples of suitable commercially available, ultraviolet-activated and visible light-activated photoinitiators have tradenames such as IRGACURE 651, IRGACURE 184, IRGACURE 369, IRGACURE 819, DAROCUR 4265 and DAROCUR 1173 commercially available from Ciba Specialty Chemicals, Tarrytown, N.Y. and LUCIRIN TPO and LUCIRIN TPO-L commercially available from BASF (Charlotte, N.C.)

A photosensitizer may also be included in a suitable initiator system. Representative photosensitizers have carbonyl groups or tertiary amino groups or mixtures thereof. Photosensitizers having a carbonyl groups include benzophenone, acetophenone, benzil, benzaldehyde, o-chlorobenzaldehyde, xanthone, thioxanthone, 9,10-anthraquinone, and other aromatic ketones. Photosensitizers having tertiary amines include methyldiethanolamine, ethyldiethanolamine, triethanolamine, phenylmethyl-ethanolamine, and dimethylaminoethylbenzoate. Commercially available photosensitizers include QUANTICURE ITX, QUANTICURE QTX, QUANTICURE PTX, QUANTICURE EPD from Biddle Sawyer Corp.

In general, the amount of photosensitizer or photoinitiator system may vary from about 0.01 to 10% by weight.

Examples of cationic initiators that may be employed include salts of onium cations, such as arylsulfonium salts, as well as organometallic salts such as ion arene systems.

Examples of free radical initiators that may be employed include azo-type initiators such as 2-2'-azobis(dimethyl-valeronitrile), azobis(isobutyronitrile), azobis(cyclohexane-nitrite), azobis(methyl-butyronitrile), and the like, peroxide initiators such as benzoyl peroxide, lauroyl peroxide, methyl ethyl ketone peroxide, isopropyl peroxy-carbonate, 2,5-dienethyl-2,5-bas(2-ethylhexanoyl-peroxy)hexane, di-tert-butyl peroxide, cumene hydroperoxide, dichlorobenzoyl peroxide, potassium persulfate, ammonium persulfate, sodium bisulfate, combination of potassium persulfate, sodium bisulfate and the like, and mixtures thereof. Of course, any other suitable free radical initiators may be employed. An effective quantity of an initiator is generally within the range of from about 0.1 percent to about 15 percent by weight of the reaction mixture, such as from 0.1 percent to about 10 percent by weight or from about 0.1 percent to about 8 percent by weight of the reaction mixture.

In various embodiments, one or more monomers are diluted prior to undergoing polymerization.

The polymer resulting from the polymerization reaction may have any suitable molecular weight. In various embodiments, the polymer has an average molecular weight (Mw) of between 10,000 and 1,000,000 Daltons, such as between 10,000 and 250,000 Daltons. One of skill in the art will understand that the amount of initiator, reaction time, reaction temperature, and the like may be varied to adjust the molecular weight of the resulting polymer.

(Meth)acrylate monomers, (meth)acrylamide monomers, or other suitable monomers may be synthesized as known in the art or obtained from a commercial vendor, such as Polysciences, Inc., Sigma Aldrich, Inc., and Sartomer, Inc.

The polypeptide may be conjugated to the polymer in any suitable manner. In some embodiments a monomer is derivatized to include the polypeptide and, thus, the polypeptide is incorporated into the polymer as it is being formed. In some embodiments, the polypeptide is grafted to the polymer after the polymer is formed.

Figure 2:
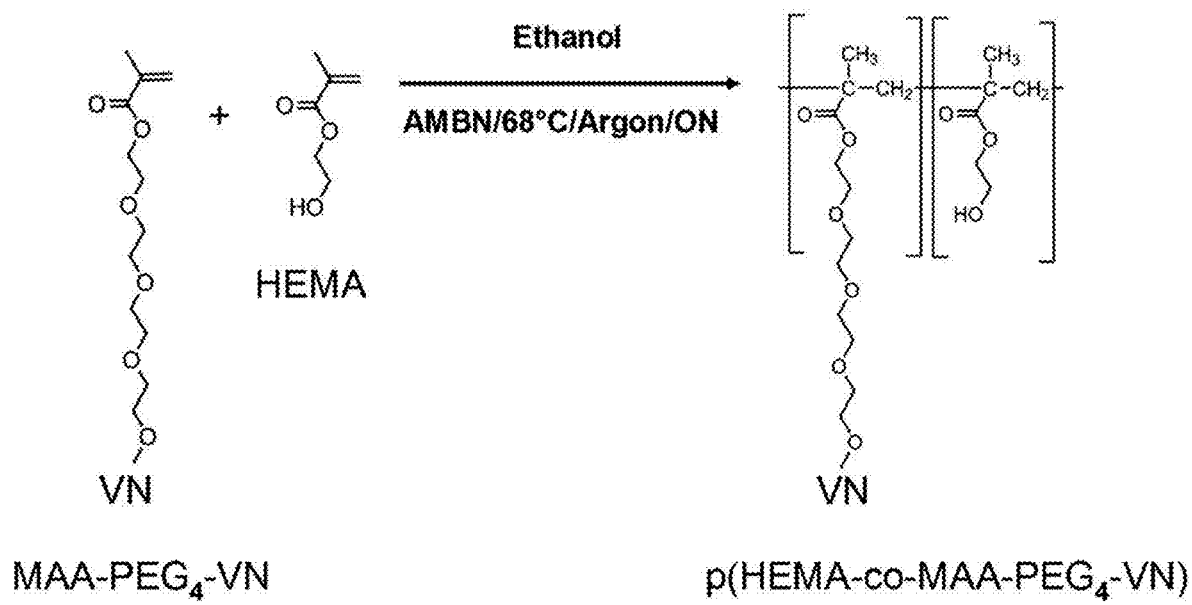
FIG. 2 is a reaction scheme for making a poly(HEMA-co-MAA-PEG4-VN) copolymer having a conjugated cell adhesive polypeptide.

Referring now to FIGS. 1-2 examples of reaction schemes for incorporating a polypeptide into a polymer as it is being formed is shown. In FIG. 1, a vitronectin polypeptide (VN) is conjugated to methacrylate (MAA) via a repeating polyethylene glycol ($PEG_4$) spacer. A homopolymer is produced by polymerizing the monomer (MMA) that is conjugated to the polypeptide (VN) under appropriate conditions. In the depicted embodiment, ethanol is the solvent, 2,2'-Azodi(2-methylbutyronitrile) (AMBN) is the thermal initiator, the reaction temperature is 68° C., and the reaction is carried out under argon.

A monomer may be derivatized to include a polypeptide using any suitable process, such as described in Example 1 presented herein. Well known processes for preparing polypeptide-monomers are described in US2007/0190036, published on Aug. 16, 2007, naming Kizilel, S., et al. as inventors. Of course, other methods for derivatizing a monomer with a polypeptide may be used.

In the embodiment depicted in FIG. 2, a copolymer is formed from 2-hydroxyethylmethacrylate (HEMA) and MMA-$PEG_4$-VN under similar reaction conditions to those described with regard to FIG. 1 above. The use of multiple monomers to produce the polymer allows one to more readily tune the properties of the resulting polymer as desired, regardless of whether the polypeptide is incorporated into the polymer as the polymer is formed.

In embodiments, a peptide monomer peptide is described by formula 1:

$$R_m\text{-}S_p\text{-}C_{ap},\quad\text{Formula 1:}$$

where, R is a polymerization moiety, "m" is an integer greater than or equal to 1, $S_p$ is an optional spacer, and $C_{ap}$ is a cell adhesive polypeptide (e.g., as described below). R may be an α,β-unsaturated group or ethylenically unsaturated group which includes acrylate, methacrylate, acrylamide, methacrylamide, maleimide or a fumarate, which is capable of polymerizing in the presence of an external energy source. In embodiments, the functionalized peptide has a polymerization moiety R which may be a photopolymerizable moiety or a thermal polymerizable moiety.

In embodiments, $S_p$ may be a polyalkylene oxide including for example polyethylene glycol (PEG) or polypropylene glycol (PPG) which are represented by the formula $(O\text{—}CH_2CHR')_{m2}$ where R' is H or $CH_3$ and m2 is an integer from 0 to 200, such as 0 to 100 or 0 to 20. The spacer may be a hydrophilic spacer, for example, polyethelene oxide (PEO). In embodiments, the spacer is $PEO_4$. In embodiments, relatively short chains of polyalkylene oxide are desirable. For example, in embodiments, $S_p$ may be $PEG_2$, $PEG_4$, $PEG_6$, $PEG_8$, $PEG_{10}$, $PEG_{12}$ or $PPG_2$, $PPG_4$, $PPG_6$, $PPG_8$, $PPG_{10}$, $PPG_{12}$ or $PPG_{20}$. In embodiments, the spacer is a polyethylene oxide with 20 or fewer repeating units (i.e. $PEG_4$, $PEG_6$, $PEG_8$, $PEG_{10}$, $PEG_{12}$, $PEG_{14}$, PEG-16, PEG-18 or $PEG_{20}$). In embodiments $S_p$ is PPG or PEG having a functional group. For example, the PEG or PPG spacer may have a maleimide, thiol, amine, silane, aldehyde, epoxide, isocyanate, acrylate or carboxyl group. In embodiments the PEG spacer is a Jeffamine, a PEG having an amine functional group. In additional embodiments, the PEG or PPG may be branched. For example the branched PEG or PPO may be a Y-branched or star-PEG or PPG. In embodiments these branched PEG or PPO spacers may allow multiple peptides to be conjugated to a base material through a single functional peptide.

Once a cell culture surface is formed (discussed below in more detail), the spacer may act to extend the peptide ($C_{ap}$) away from the cell culture surface, making the peptide more accessible to cells in culture, and improving the efficiency of the surface for cell culture. In addition, hydrophilic spacers may act to repel proteins, preventing non-specific absorption of cells or proteins to the functionalized peptide. In embodiments, the use of a cell adhesive peptide with a spacer such as PEO (polyethylene oxide) in preparing cell culture articles allows for the preparation of such articles using a lower overall concentration of adhesive peptide.

In embodiments, $S_p$ may be an amino acid $Xaa_n$ where Xaa is independently any amino acid and n is an integer from 0 to 30, from 0 to 10, from 0 to 6 or from 0 to 3. For example, in embodiments, $S_p$ may be an amino acid $Xaa_n$ where Xaa is G and where n=1 to 20, or $S_p$ may be an amino acid $Xaa_n$ where Xaa is K and n=1 to 20, or $S_p$ may be an amino acid $Xaa_n$ where Xaa is D and n=1 to 20, or $S_p$ may be an amino acid $Xaa_n$ where Xaa is E and n=1 to 20. In embodiment, spacer $S_p$ may be a three amino acid sequence such as LysGlyGly or LysTyrGly. In embodiments, $Xaa_n$ is a series of the same amino acid. In embodiments, the spacer $S_p$ may be combinations of $Xaa_n$ and polyethylene or polypropylene oxide. $Xaa_n$ may comprise a hydrophilic amino acid such as lysine, glycine, glutamic acid, aspartic acid or arginine amino acid. In embodiments, $Xaa_n$ may have a terminal lysine or arginine. Or, in embodiments, the spacer $S_p$ may comprise polyethylene oxide spacer and amino acid spacer in any combination. In embodiments, $S_p$ may be a hydrophobic spacer such as palmitic acid, stearic acid, lauric acid or hexaethylene diamine. In embodiments, $S_p$ may be carboxyethyl methacrylate.

The polymerization moiety may attach to the spacer, $S_p$, in any suitable manner such as through polyethylene oxide, through the side chain of an amino acid such as lysine, at the N-terminus of the amino acid, or the like. Amino acid $Xaa_n$ may be acetylated and/or amidated to protect it from degradation. However, if $Xaa_n$ is acetylated, the polymerization moiety cannot be bound to $Xaa_n$ through the N-terminus of the amino acid. For example, a methacrylic acid may be bound to a lysine amino acid through the side chain of the lysine amino acid where $S_p$ is $Xaa_n$, Xaa is lysine, n=1, and $R_m$ is methacrylic acid.

In embodiments, the spacer $S_p$ is $Xaa_n$ and $Xaa_n$ has a terminal lysine. In embodiments, $Xaa_n$ may be bound to a polymerization moiety $R_m$. For example, $Xaa_n$ may be (MAA)LysGlyGly or (MAA)LysTyrGly, where MAA is the polymerization moiety methacrylic acid (MAA) bound to $Xaa_n$ through the side chain of the terminal lysine amino acid. In additional embodiments, the polymerization moiety may be bound to the N-terminus of the $Xaa_n$ amino acid or amino acid chain, if the N-terminus is not acetylated. Each functionalized peptide has at least one polymerization moiety, and may have more than one.

In various embodiments, a polypeptide is grafted to a polymer that has already been formed. Preferably, polypeptide includes an amino acid capable of conjugating to a pendant reactive group of the polymer. Examples of reactive groups that the polymer may have for reaction with a polypeptide include maleimide, glycidyl, isocyanate, isothiocyante, activated esters, activated carbonates, anhydride, and the like. By way of example, any native or biomimetic amino acid having functionality that enables nucleophilic addition; e.g. via amide bond formation, may be included in polypeptide for purposes of conjugating to the polypeptide having a suitable reactive group. Lysine, homolysine, ornithine, diaminoproprionic acid, and diaminobutanoic acid are examples of amino acids having suitable properties for conjugation to a reactive group of the polymer, such as carboxyl group. In addition, the N-terminal alpha amine of a polypeptide may be used to conjugate to the carboxyl group, if the N-terminal amine is not capped. In various embodiments, the amino acid of polypeptide that conjugates with the polymer is at the carboxy terminal position or the amino terminal position of the polypeptide.

A polypeptide may be conjugated to the polymer via any suitable technique. A polypeptide may be conjugated to a polymer via an amino terminal amino acid, a carboxy terminal amino acid, or an internal amino acid. One suitable technique involves 1-ethyl-3-[3-dimethylaminopropyl] carbodiimide hydrochloride (EDC)/N-hydroxysuccinimide (NHS) chemistry, as generally known in the art. EDC and NHS or N-hydroxysulfosuccinimide (sulfo-NHS) can react with free carboxyl groups of the polymer to produce amine reactive NHS esters. EDC reacts with a carboxyl group of the polymer to produce an amine-reactive O-acylisourea intermediate that is susceptible to hydrolysis. The addition of NHS or sulfo-NHS stabilizes the amine-reactive O-acylisourea intermediate by converting it to an amine reactive NHS or sulfo-NHS ester, allowing for a two-step procedure. Following activation of the polymer, the polypeptide may then be added and the terminal amine of the polypeptide can react with the amine reactive ester to form a stable amide bond, thus conjugating the polypeptide to the polymer layer. When EDC/NHS chemistry is employed to conjugate a polypeptide to the polymer, the N-terminal amino acid is preferably an amine containing amino acid such as lysine, ornithine, diaminobutyric acid, or diaminoproprionic acid. Of course, any acceptable nucleophile may be employed, such as hydroxylamines, hydrazines, hydroxyls, and the like.

EDC/NHS chemistry results in a zero length crosslinking of polypeptide to polymer. Linkers or spacers, such as poly(ethylene glycol) linkers (e.g., available from Quanta BioDesign, Ltd.) with a terminal amine may be added to the N-terminal amino acid of polypeptide. When adding a linker to the N-terminal amino acid, the linker is preferably a N-PG-amido-PEGx-acid where PG is a protecting group such as the Fmoc group, the BOC group, the CBZ group or any other group amenable to peptide synthesis and X is 2, 4, 6, 8, 12, 24 or any other discrete PEG which may be available. Of course, any other suitable mechanism for grafting the polypeptide to the polymer may be used.

Regardless of how the polypeptide is conjugated to the polymer; e.g., via incorporation of a derivitized monomer conjugated to the polypeptide or via grafting, the ratio of monomers to which the polypeptide is attached or is to be attached (peptide-monomer) to monomers to which no polypeptide is attached or is to be attached (nonpeptide-monomer) may be varied to achieve desired properties, such as swellability, water solubility, modulus, and the like. In embodiments, the molar ratio of peptide monomer to nonpeptide monomer is from about 1:1 to about 1:50, such as from about 1:5 and 1:20, about 1:10, about 1:9 or the like.

In embodiments, the polypeptide is conjugated to the polymer via a linker or spacer. A linker or spacer, such as a repeating poly(ethylene glycol) linker, or any other suitable linker, may be used to increase distance from polypeptide to surface of polymer. The linker may be of any suitable length. For example, if the linker is a repeating poly(ethylene glycol) linker, the linker may contain between 2 and 10 repeating ethylene glycol units. In some embodiments, the linker is a repeating poly(ethylene glycol) linker having about 4 repeating ethylene glycol units. All, some, or none of the polypeptides may be conjugated to a polymer via linkers. Other potential linkers that may be employed include polypeptide linkers such as poly(glycine) or poly(β-alanine).

A linker may serve to provide better accessibility of the polypeptide to cells when used in cell culture. In addition, the use of a linker in embodiments where the polypeptide is conjugated to a monomer, the efficiency of polymerization of the monomer into a homopolymer or copolymer may be increased.

The polypeptide may be cyclized or include a cyclic portion. Any suitable method for forming cyclic polypeptide may be employed. For example, an amide linkage may be created by cyclizing the free amino functionality on an appropriate amino-acid side chain and a free carboxyl group of an appropriate amino acid side chain. Also, a disulfide linkage may be created between free sulfydryl groups of side chains appropriate amino acids in the peptide sequence. Any suitable technique may be employed to form cyclic polypeptides (or portions thereof). By way of example, methods described in, e.g., WO1989005150 may be employed to form cyclic polypeptides. Head-to-tail cyclic polypeptides, where the polypeptides have an amide bond between the carboxy terminus and the amino terminus may be employed. An alternative to the disulfide bond would be a diselenide bond using two selenocysteines or mixed selenide/sulfide bond, e.g., as described in Koide et al, 1993, Chem. Pharm. Bull. 41(3):502-6; Koide et al., 1993, Chem. Pharm. Bull. 41(9):1596-1600; or Besse and Moroder, 1997, Journal of Peptide Science, vol. 3, 442-453.

Polypeptides may be synthesized as known in the art (or alternatively produced through molecular biological techniques) or obtained from a commercial vendor, such as American Peptide Company, CEM Corporation, or GenScript Corporation. Linkers may be synthesized as known in the art or obtained from a commercial vendor, such as discrete polyethylene glycol (dPEG) linkers available from Quanta BioDesign, Ltd.

In various embodiments, the polypeptide, or a portion thereof, has cell adhesive activity; i.e., when the polypeptide is conjugated to the polymer, the polypeptide allows a cell to adhere to the surface of the peptide-containing polymer. By way of example, the polypeptide may include an amino sequence, or a cell adhesive portion thereof, recognized by proteins from the integrin family or leading to an interaction with cellular molecules able to sustain cell adhesion. For example, the polypeptide may include an amino acid sequence derived from collagen, keratin, gelatin, fibronectin, vitronectin, laminin, bone sialoprotein (BSP), or the like, or portions thereof. In various embodiments, polypeptide includes an amino acid sequence of ArgGlyAsp (RGD).

Examples of peptides that may be used in embodiments herein are listed in Table 1.

TABLE 1

Non-limiting examples of polypeptides

| Sequence | Source |
|---|---|
| KGGGQKCIVQTTSWSQCSKS (SEQ ID NO: 1) | Cyr61 res 224-240 |
| GGGQKCIVQTTSWSQCSKS (SEQ ID NO: 2) | Cyr61 res 224-240 |
| KYGLALERKDHSG (SEQ ID NO: 3) | TSP1 res 87-96 |
| YGLALERKDHSG (SEQ ID NO: 4) | TSP1 res 87-96 |
| KGGSINNNRWHSIYITRFGNMGS (SEQ ID NO: 5) | mLMα1 res 2179-2198 |
| GGSINNNRWHSIYITRFGNMGS (SEQ ID NO: 6) | mLMα1 res 2179-2198 |
| KGGTWYKIAFQRNRK (SEQ ID NO: 7) | mLMα1 res 2370-2381 |
| GGTWYKIAFQRNRK (SEQ ID NO: 8) | mLMα1 res 2370-2381 |
| KGGTSIKIRGTYSER (SEQ ID NO: 9) | mLMγ1 res 650-261 |
| GGTSIKIRGTYSER (SEQ ID NO: 10) | mLMγ1 res 650-261 |
| KYGTDIRVTLNRLNTF (SEQ ID NO: 11) | mLMγ1 res 245-257 |
| YGTDIRVTLNRLNTF (SEQ ID NO: 12) | mLMγ1 res 245-257 |
| KYGSETTVKYIFRLHE (SEQ ID NO: 13) | mLMγ1 res 615-627 |
| YGSETTVKYIFRLHE (SEQ ID NO: 14) | mLMγ1 res 615-627 |
| KYGKAFDITYVRLKF (SEQ ID NO: 15) | mLMγ1 res 139-150 |
| YGKAFDITYVRLKF (SEQ ID NO: 16) | mLMγ1 res 139-150 |
| KYGAASIKVAVSADR (SEQ ID NO: 17) | mLMα1 res 2122-2132 |
| YGAASIKVAVSADR (SEQ ID NO: 18) | mLMα1 res 2122-2132 |
| CGGNGEPRGDTYRAY (SEQ ID NO: 19) | BSP |
| GGNGEPRGDTYRAY (SEQ ID NO: 20) | BSP |
| CGGNGEPRGDTRAY (SEQ ID NO: 21) | BSP-Y |
| GGNGEPRGDTRAY (SEQ ID NO: 22) | BSP-Y |
| KYGRKRLQVQLSIRT (SEQ ID NO: 23) | mLMα1 res 2719-2730 |
| YGRKRLQVQLSIRT (SEQ ID NO: 24) | mLMα1 res 2719-2730 |
| KGGRNIAEIIKDI (SEQ ID NO: 25) | LMβ1 |
| GGRNIAEIIKDI (SEQ ID NO: 26) | LMβ1 |
| KGGPQVTRGDVFTMP (SEQ ID NO: 27) | VN |
| GGPQVTRGDVFTMP (SEQ ID NO: 28) | VN |
| GRGDSPK (SEQ ID NO: 29) | Short FN |
| KGGAVTGRGDSPASS (SEQ ID NO: 30) | Long FN |
| GGAVTGRGDSPASS (SEQ ID NO: 31) | Long FN |
| Yaa₁PQVTRGNVFTMP (SEQ ID NO: 32) | VN |
| RGDYK (SEQ ID NO: 33) | RGD |

For any of the polypeptides discussed herein, it will be understood that a conservative amino acid may be substituted for a specifically identified or known amino acid. A "conservative amino acid", as used herein, refers to an amino acid that is functionally similar to a second amino acid. Such amino acids may be substituted for each other in a polypeptide with a minimal disturbance to the structure or function of the polypeptide according to well-known techniques. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q).

One or more polypeptide may be conjugated to a polymer, whether grafted or incorporated during polymer formation, in any suitable amount. Preferably, weigh percentage of the polypeptide is sufficiently high to render the polymer conjugated to the polymer water soluble. In various embodiments, the weight percentage of the polypeptide relative to the polymer conjugated to the polypeptide is 10% or greater, 20% or greater, 40% or greater, 60% or greater, or the like. Such weight percentages have been determined to achieve good water solubility, immobilization efficiency and acceptable cell adhesion for polypeptides having a molecular weight of 1500 Daltons or higher.

Polymers as described herein provide a synthetic surface to which any suitable adhesion polypeptide or combinations of polypeptides may be conjugated, providing an alternative to biological substrates or serum that have unknown components. In current cell culture practice, it is known that some cell types require the presence of a biological polypeptide or combination of peptides on the culture surface for the cells to adhere to the surface and be sustainably cultured. For example, HepG2/C3A hepatocyte cells can attach to plastic culture ware in the presence of serum. It is also known that serum can provide polypeptides that can adhere to plastic culture ware to provide a surface to which certain cells can attach. However, biologically-derived substrates and serum contain unknown components. For cells where the particular component or combination of components (peptides) of serum or biologically-derived substrates that cause cell attachment are known, those known polypeptides can be synthesized and applied to a polymer as described herein to allow the cells to be cultured on a synthetic surface having no or very few components of unknown origin or composition.

Cell Culture Medium Composition

The polymer conjugated to the polypeptide may be dissolved in an aqueous solution for use in coating cell culture articles or culturing cells. In embodiments, the aqueous solution is free, or substantially free, of organic solvents. It will be understood that some minor amounts of organic solvents may be present in the aqueous solution, for example as a result some organic solvent remaining in the polymer after polymerization. As used herein, "substantially free," as it relates to an organic solvent in an aqueous solution, means that the aqueous solution comprises less than 2% of the organic solvent by weight. In many embodiments, the aqueous solution contains less than 1%, less than 0.5%, less that 0.2% or less that 0.1% of an organic solvent. Examples of organic solvents from which the aqueous solution is free include methanol, ethanol, butanol, propanol, octanol, hexane, heptane, acetone, acetyl acetate, ethyl acetate, dimethylformamide (DMF), dimethylsulfoxide (DMSO), and the like.

The polymer conjugated to the polypeptide may be dissolved in the aqueous solution at any suitable concentration for purposes of coating or culture. For example, the aqueous solution may contain between 0.001 mg/ml and 1 mg/ml of the polymer conjugated to the polypeptide, such as between 0.003 mg/ml and 0.05 mg/ml of the polymer conjugated to the polypeptide.

In embodiments, the aqueous solution is a cell culture medium solution, meaning that the solution is configured to support the culture of cells, such as mammalian cells. In embodiments, the cells are stem cells, such as human embryonic stem cells or human mesenchymal stem cells. The cell culture medium solution may have a pH of between about 7 and about 8, such as between about 7.2 and 7.5, which may be buffered by a pH buffer, such as phosphate buffer, citrate buffer, or the like. The cell culture medium solution may include any components suitable for cell culture, such as glucose, amino acids, vitamins, inorganic salts or the like. Cell culture constituents and concentrations are known in the art. See, for example, Burgener A, Butler. "Medium Development". In *Cell Culture Technology For Pharmaceutical and Cell-Based Therapies*. Edited by Ozturk SS and Hu WS. 2006. In embodiments, the cell culture medium includes d-glucose.

Examples of various components that may be included in a cell culture medium and concentrations of the components in the medium are provided below. By way of example, the cell culture medium may comprise from about 1 mM d-glucose to about 50 mM d-glucose, such as from about 2 mM to about 30 mM d-glucose. Examples of amino acids that may be included in the cell culture medium include l-arginine, l-cystine, l-histidine, l-isoleucine, l-leucine, l-lysine, l-methionine, l-phenylaline, l-threonine, l-tryptophan, l-tyrosine, l-valine or the like. The amino acids may be present at any suitable concentration, such as from about $1\times10^{-3}$ mM to about 20 mM. It will be understood that the concentration of the amino acid may vary depending on the amino acid. Inorganic salts may be included in the cell culture medium at appropriate concentrations. Examples of suitable inorganic salts include calcium chloride, calcium nitrate, cupric sulfate, ferric nitrate, ferrous sulfate, potassium chloride, magnesium chloride, magnesium sulfate, sodium chloride, sodium bicarbonate, sodium phosphate, and the like.

In embodiments, the polymer-polypeptide is dissolved in a commercially available cell culture medium, such as DMEM (Dulbecco's Modified Eagle Medium) such as available from GIBCO; StemPro® a fully defined, serum- and feeder-free medium (SFM) specially formulated for the growth and expansion of human embryonic stem cells (hESCs), available from Invitrogen.; mTeSR™1 maintenance media for human embryonic stem cells, available from StemCell Technologies, Inc.; MesenCult®-XF medium, which is a standardized, xeno-free, serum-free medium for the culture of human mesenchymal stem cells, available from StemCell Technologies Inc.; or the like.

In embodiments, the cell culture medium is a chemically-defined medium. Because all components of chemically-defined media have a known chemical structure or are formed from components of known structure (e.g., synthetic polymers formed from monomers of known structure), variability in culture conditions and thus cell response can be reduced, increasing reproducibility. In addition, the possibility of contamination is reduced. Further, the ability to scale up is made easier due, at least in part, to the factors discussed above. Chemically defined cell culture media are commercially available from Invitrogen (Invitrogen Corporation, 1600 Faraday Avenue, PO Box 6482, Carlsbad, Calif. 92008) as StemPro® a fully defined, serum- and feeder-free medium (SFM) specially formulated for the growth and expansion of human embryonic stem cells (hESCs) and StemCell Technologies, Inc. as mTeSR™1 maintenance media for human embryonic stem cells. MesenCult®-XF Medium is another example of a chemically-defined medium available from STEMCELL Technologies Inc.

In embodiments, the cell culture medium is conditioned medium to which a polymer-polypeptide has been added.

In embodiments, the aqueous solution, such as cell culture medium solution, is free or substantially free of cross-linking agents. As used herein, "cross-linking agent" refers to an agent capable of inducing cross-linking in, or capable of cross-linking, the polymer portion of the polymer-polypeptide. As used herein, "substantially free" as it relates to cross-linking agents, means that no appreciable crosslinking occurs in the polymer as a result of the presence of trace amounts of a crosslinking agent. Examples of cross-linkers that the polymer portion is substantially free from include well known crosslinking agents include homo-multifunctional or hetero-multifunctional crosslinking agent as those described in "Bioconjugate Techniques, Second Edition by Greg T. Hermanson". In embodiments, the composition is also "substantially free" of multifunctional oligomers and polymers that could lead to formation of interpenetrated network or semi-interpenetrated network.

The cell culture medium containing the polymer having conjugated polypeptide may be sterilized in any suitable manner. In embodiment, the polymer-polypeptide is sterilized via gamma radiation; e.g. as a dry powder, and added to sterilized cell culture medium using aseptic technique. Gamma or e-beam radiation, rather than filter sterilization as used with naturally occurring or animal derived extracellular matrix proteins, may be beneficially used with the synthetic polymer-polypeptides described herein. Of course, filter sterilization may be employed if desired.

The cell culture medium containing the polymer having conjugated polypeptide may be stored at room temperature (25° C.) or below to keep the polymer-polypeptide in solution. By way of example, the medium may be refrigerated (about 5° C.) for storage. Refrigeration may also serve to prolong the shelf-life of the medium.

Coating Process

The polymer conjugated to the polypeptide may be coated onto a cell culture article in any suitable manner. Generally, an aqueous solution, such as a cell culture medium, containing the polymer conjugated to the polypeptide, as described above, is disposed on a surface of the cell culture article. The polymer conjugated to the polypeptide is then incubated with the cell culture article in the aqueous solution under cell culture conditions, such as at 37° C., about 25° C. or the like, until the polymer conjugated to the polypeptide attaches to the surface of the cell culture article. In embodiments, the attachment process begins immediately, within seconds or minutes.

While it is possible that the polymer covalently attaches to the surface of the article, the polymer will typically be attached to the article via non covalent interactions. Examples of non-covalent interactions that may attach the polymer with the substrate include chemical adsorption, hydrogen bonding, surface interpenetration, ionic bonding, van der Waals forces, hydrophobic interactions, dipole-dipole interactions, mechanical interlocking, and combinations thereof.

Preferably, the polymer attaches to and coats the surface of the article during cell culture conditions, such as in the presence of cell culture media at 37° C. Because the polymer-polypeptide is stable in, and compatible with, cell culture medium, it is acceptable for some of the polymer-polypeptide to remain in the medium or for equilibrium between attached and unattached polymer-polypeptide to exist. Preferably upon replenishment of medium; e.g., removal of used medium and replacement with new medium (e.g., without polymer-polypeptide), the attached polymer-polypeptide remains attached to the substrate. In embodiments, 90% or more, such as 95% or more or 99% or more, of the previously attached polymer-polypeptide remains attached during medium replacement. In embodiments, replacement medium may include an appropriate concentration of polymer-polypeptide to maintain a desired equilibrium polymer-peptide coating on substrate on the substrate.

Without intending to be bound to any particular theory, it is believed that the high percentage of polypeptide relative to the polymer aids in the surprising adsorption of the polymer on appropriate substrates from an aqueous solution and its non-solubility in water after adsorption. The high polypeptide content may lead to a high density of hydrogen bonding between polypeptides, inducing physical crosslinking or aggregation, which is a behaviour similar to natural occurring proteins. It is also well-known that some specific polypeptides are soluble in aqueous solution below their transition temperature, but they hydrophobically collapse and aggregate when the temperature is raised above the transition temperature. Such hydrophobic collapse may play a role in adsorption of polymers conjugated with polypeptides that are subjected to cell culture conditions, such as 37° C.

The surface of the cell culture article to which the polymer conjugated to the polypeptide is coated may be formed of any suitable material. For example, the surface of the cell culture article may be formed from a ceramic substance, a glass, a plastic, a polymer or co-polymer, any combinations thereof, or a coating of one material on another. Such base materials include glass materials such as soda-lime glass, pyrex glass, vycor glass, quartz glass; silicon; plastics or polymers, including dendritic polymers, such as poly(vinyl chloride), poly(vinyl alcohol), poly(methyl methacrylate), poly(vinyl acetate-co-maleic anhydride), poly(dimethylsiloxane) monomethacrylate, cyclic olefin polymers, fluorocarbon polymers, polystyrenes, polypropylene, polyethyleneimine; copolymers such as poly(vinyl acetate-co-maleic anhydride), poly(styrene-co-maleic anhydride), poly(ethylene-co-acrylic acid) or derivatives of these or the like.

In embodiments, the surface of the cell culture article to which the polymer-polypeptide attaches has a water contact angle (sessile drop measurement) of from about 0 to about 100, such as from about 0 to about 50, from about 0 to about 30, from about 12° to about 85°, from about 25° to about 70°, from about 30° to about 60°, or the like. It will be understood that substrates may be treated so that they exhibit an appropriate contact angle. For example, the substrate may be corona treated or plasma treated. Examples of vacuum or atmospheric pressure plasma include RF and microwave plasmas both primary and secondary, dielectric barrier discharge, and corona discharge generated in molecular or mixed gases including air, oxygen, nitrogen, argon, carbon dioxide, nitrous oxide, or water vapor. By way of example, plasma treated polystyrene, such as TCT polystyrene or CellBIND® treated polystyrene provide good substrates for polymer-polypeptide attachment. Naturally occurring animal-derived biological adhesive proteins also exhibit good binding to such surfaces. Accordingly, surfaces to which naturally occurring proteins readily attach may also provide good substrates for polymer-polypeptide attachment.

Cell Culture Article

A polymer conjugated to a polypeptide as described herein may be attached to the surface of any suitable cell culture article, such as single and multi-well plates, such as 6, 12, 96, 384, and 1536 well plates, jars, petri dishes, flasks, beakers, plates, microcarriers such as glass or polymer beads, roller bottles, slides, such as chambered and multi-chambered culture slides, tubes, cover slips, bags, membranes, hollow fibers, beads and microcarriers, cups, spinner bottles, perfusion chambers, bioreactors, CellSTACK® and fermenters.

Figure 3A:
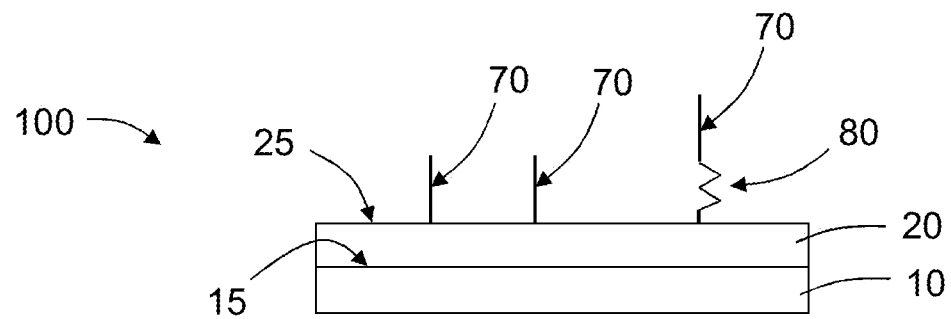
FIGS. 3A-B are schematic diagrams of side views of coated articles.

Referring to FIG. 3A, a schematic diagram of a side view of an article 100 for culturing cells is shown. The article 100 includes a base material substrate 10 having a surface 15. A polymer 20 conjugated to a polypeptide 70 is disposed on the surface 15 of the base material 10. As depicted, the polypeptide 70 may be conjugated or covalently bound to the polymer 20 directly or indirectly via linker 80 as described above. While not shown, it will be understood that the polymer 20 conjugated to the polypeptide 70 may be disposed on a portion of base material 10. The base material 10 may be any material suitable for culturing cells, such as those described above.

Figure 3B:
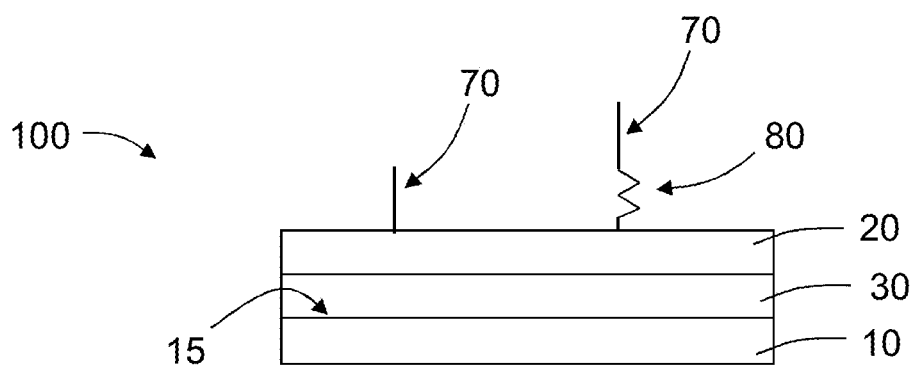

As shown in FIG. 3B, an intermediate layer 30 may be disposed between surface 15 of base material 10 and the coated polymer 20 conjugated to the polypeptide 70. Intermediate layer 30 may be configured to improve binding of the coated polymer 20 conjugated to the polypeptide 70 to the substrate 10, to facilitate spreading of the aqueous solution containing the polymer conjugated to the polypeptide, to render portions of the surface 10 that are uncoated cytophobic to encourage cell growth on coated areas, to provide topographical features if desired through, for example, patterned printing, or the like. For example, if substrate 10 is a glass substrate, it may be desirable to treat a surface of the glass substrate with an epoxy coating or a silane coating. For various polymer base materials 10 it may be desirable to provide an intermediate layer 30 of polyamide, polyimide, polypropylene, polyethylene, or poly-acrylate. While not shown, it will be understood that the coated polymer 20 conjugated to the polypeptide 70 may be disposed on a portion of intermediate layer 30. It will be further understood that intermediate layer 30 may be disposed on a portion of base material 10.

Figure 4A:
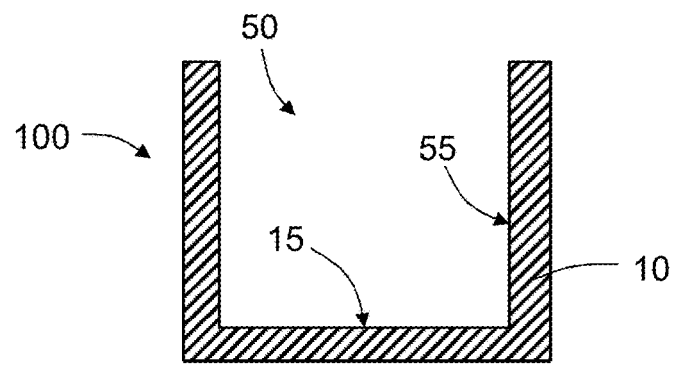
FIGS. 4A-C are schematic diagrams of cross sections of cell culture articles having a well. Uncoated FIG. 4A; coated surface FIG. 4B; and coated surface and side walls FIG. 4C.

Article 100, in numerous embodiments, is cell culture ware having a well, such as a Petri dish, a multi-well plate, a flask, a beaker or other container having a well. Referring now to FIG. 4, article 100 formed from base material 10 may include one or more wells 50. Well 50 includes a sidewall 55 and a surface 15.

Figure 4B:
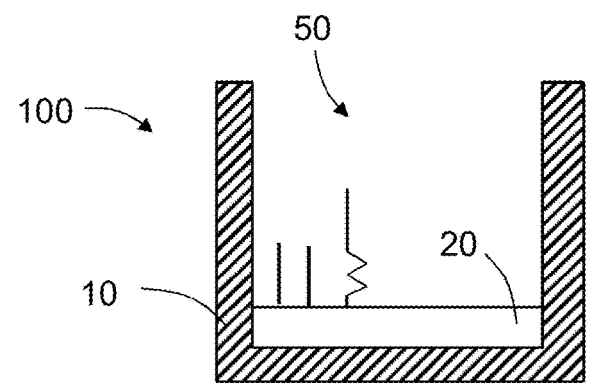
Figure 4C:
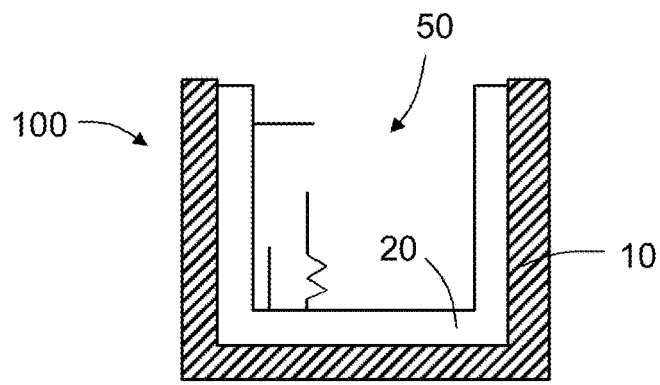

Referring to FIG. 4B-C, a polymer 20 conjugated to a polypeptide 70 may be disposed on surface 15 or sidewalls 55 (or, as discussed above with regard to FIG. 1 one or more intermediate layer 30 may be disposed between surface 15 or sidewall 55 and coated polymer 20 conjugated to the polypeptide 70) or a portion thereof. As shown in FIG. 4C, sidewalls 55 may be coated with polymer 20 conjugated to polypeptide 70.

In various embodiments, surface 15 of base material 10 is treated, either physically or chemically, to impart a desirable property or characteristic to the surface 15. For example, and as discussed above, surface 15 may be corona treated or plasma treated.

In embodiments, the coated polymer 20 conjugated to the polypeptide 70, whether disposed on an intermediate layer 30 or base material 10, uniformly coats the underlying substrate. By "uniformly coated", it is meant that the layer 20 in a given area, for example a surface of a well of a culture plate, completely coats the area at a thickness of about 5 nm or greater. While the thickness of a uniformly coated surface may vary across the surface, there are no areas of the uniformly coated surfaces through which the underlying layer (either intermediate layer 30 or base material 10) is exposed. Cell responses across non-uniform surfaces tend to be more variable than cell responses across uniform surfaces.

In various embodiments, article 100 includes a uniformly coated layer 20 having a surface 25 with an area greater than about 5 mm$^2$. When the area of the surface 15 is too small, reliable cell responses may not be readily observable because some cells, such as human embryonic stem cells, are seeded as colonies or clusters of cells (e.g., having a diameter of about 0.5 mm) and adequate surface is desirable to ensure attachment of sufficient numbers of colonies to produce a quantitative cell response. In numerous embodiments, an article 100 has a well 50 having a uniformly coated surface 15, where the surface 15 has an area greater than about 0.1 cm$^2$, greater than about 0.3 cm$^2$, greater than about 0.9 cm$^2$, or greater than about 1 cm$^2$.

Incubating Cells on Synthetic Polymer Containing Conjugated Polypeptide

A cell culture article having a polymer containing a conjugated polypeptide as described above may be seeded with cells. In embodiments, the cells are introduced into cell culture medium that includes the polymer-polypeptide as discussed above. During the cell culture process, the polymer conjugated to the polypeptide coats a surface of the cell culture article.

Without intending to be bound by theory, it is believed that cell-cell interaction may be enhanced by including the polymer-polypeptide in the cell seeding culture medium. That is, cell-cell interaction may occur in the medium, and may be encouraged by the polymer-polypeptide in the medium, before the polymer-polypeptide attaches to the surface of the cell culture article.

Any type of cell may be used in accordance with the teachings presented herein. For example, the cells may be connective tissue cells such as epithelial and endothelial cells, hepatocytes, skeletal or smooth muscle cells, heart muscle cells, intestinal cells, kidney cells, or cells from other organs, stem cells, islet cells, blood vessel cells, lymphocytes, cancer cells, or the like. The cells may be mammalian cells, preferably human cells, but may also be non-mammalian cells such as bacterial, yeast, or plant cells.

In numerous embodiments, the cells are stem cells which, as generally understood in the art, refer to cells that have the ability to continuously divide (self-renewal) and that are capable of differentiating into a diverse range of specialized cells. In some embodiments, the stem cells are multipotent, totipotent, or pluripotent stem cells that are isolated from an organ or tissue of a subject. Such cells are capable of giving rise to a fully differentiated or mature cell types. A stem cell may be a bone marrow-derived stem cell, autologous or otherwise, a neuronal stem cell, or an embryonic stem cell. A stem cell may be nestin positive. A stem cell may be a hematopoeietic stem cell. A stem cell may be a multi-lineage cell derived from epithelial and adipose tissues, umbilical cord blood, liver, brain or other organ. In various embodiments, the stem cells are undifferentiated stem cells, such as undifferentiated embryonic stem cells.

Prior to seeding cells, the cells may be harvested and suspended in a suitable medium, such as a growth medium in which the cells are to be cultured once seeded onto the surface. As described above, the medium may include the polymer-polypeptide that will form a coating when incubated on a cell culture surface in the medium under cell culture conditions. For example, the cells may be suspended in and cultured in a serum-containing medium, a conditioned medium, or a chemically-defined medium. As used herein, "chemically-defined medium" means cell culture media that contains no components of unknown composition. Chemically defined media may, in various embodiments, contain no proteins, hydrosylates, or peptides of unknown composition. In some embodiments, conditioned media contains polypeptides or proteins of known composition, such as recombinant growth hormones. Because all components of chemically-defined media have a known chemical structure, variability in culture conditions and thus cell response can be reduced, increasing reproducibility. In addition, the possibility of contamination is reduced.

One or more growth or other factors may be added to the medium in which cells are incubated. The factors may facilitate cellular proliferation, adhesion, self-renewal, differentiation, or the like. Examples of factors that may be added to or included in the medium include muscle morphogenic factor (MMP), vascular endothelium growth factor (VEGF), interleukins, nerve growth factor (NGF), erythropoietin, platelet derived growth factor (PDGF), epidermal growth factor (EGF), activin A (ACT), hematopoietic growth factors, retinoic acid (RA), interferons, fibroblastic growth factors, such as basic fibroblast growth factor (bFGF), bone morphogenetic protein (BMP), peptide growth factors, heparin binding growth factor (HBGF), hepatocyte growth factor, tumor necrosis factors, insulin-like growth factors (IGF) I and II, transforming growth factors, such as transforming growth factor-β1 (TGFβ1), and colony stimulating factors.

The cells may be seeded at any suitable concentration. Typically, the cells are seeded at about 10,000 cells/cm$^2$ of substrate to about 500,000 cells/cm$^2$. For example, cells may be seeded at about 50,000 cells/cm$^2$ of substrate to about 150,000 cells/cm$^2$. However, higher and lower concentrations may readily be used. The incubation time and conditions, such as temperature, $CO_2$ and $O_2$ levels, growth medium, and the like, will depend on the nature of the cells being cultured and can be readily modified. The amount of time that the cells are incubated on the surface may vary depending on the cell response desired.

The cultured cells may be used for any suitable purpose, including (i) obtaining sufficient amounts of undifferentiated stem cells cultured on a synthetic surface in a chemically defined medium for use in investigational studies or for developing therapeutic uses, (ii) for investigational studies of the cells in culture, (iii) for developing therapeutic uses, and (iv) for therapeutic purposes.

Aspects

A variety of aspects of compositions, methods, and articles have been described herein. A summary of a few select examples of such compositions, methods, and articles are provided below.

In a $1^{st}$ aspect, an aqueous cell culture medium composition comprises (i) an aqueous cell culture solution configured to support the culture of mammalian cells; and (ii) a synthetic polymer conjugated to a polypeptide dissolved in the aqueous cell culture solution, wherein the synthetic polymer conjugated to a polypeptide is configured to attach to the surface of a cell culture article under cell culture conditions, and wherein incubation of the aqueous cell culture medium composition on a cell culture surface under cell culture conditions results is attachment to the surface of the synthetic polymer conjugated to the polypeptide.

A $2^{nd}$ aspect is a composition of the $1^{st}$ aspect, wherein the cell culture medium composition is a chemically defined composition.

A $3^{rd}$ aspect is a composition of the $1^{st}$ or $2^{nd}$ aspect, wherein the cell culture medium is free of animal derived components.

A $4^{th}$ aspect is an aqueous cell culture medium composition comprising (i) an aqueous cell culture solution configured to support the culture of mammalian cells; and (ii) a synthetic polymer conjugated to a polypeptide dissolved in the aqueous cell culture solution, wherein the polymer is selected from the group consisting of a polymer that has a linear backbone and is crosslink free, a polymer that has a branched backbone and is crosslink free, and a star polymer free of crosslinks, and wherein the synthetic polymer conjugated to the polypeptide is soluble in water at 20° C. or less, wherein the composition is substantially free of organic solvents, and wherein incubation of the aqueous cell culture medium composition on a cell culture surface under cell culture conditions results in attachment to the surface of the synthetic polymer conjugated to the polypeptide.

A $5^{th}$ aspect is a composition of the $4^{th}$ aspect, wherein a substantially similar polymer that is not conjugate to the polypeptide is insoluble in water at 37° C.

A $6^{th}$ aspect is a composition of the $4^{th}$ or $5^{th}$ aspects, wherein the polymer has a linear backbone and is crosslink free.

A $7^{th}$ aspect is a composition of any of aspects 4-6, wherein the cell culture medium is free of animal derived components.

An $8^{th}$ aspect is a composition of any of aspects 4-7, wherein the cell culture medium composition is a chemically defined composition.

A $9^{th}$ aspect is a composition of any of aspects 4-8, wherein the polymer is formed from no monomers having di- or higher-functionality.

An $10^{th}$ aspect is a composition of any of aspects 4-9, wherein the polymer is formed from at least one monomer comprising a conjugated polypeptide.

An $11^{th}$ aspect is a composition of the $10^{th}$ aspect, wherein the at least one monomer comprising a conjugated polypeptide is methacrylic acid.

A $12^{th}$ aspect is a composition of any of aspects 4-11, wherein the polymer is formed from polymerization of (i) methacrylic acid conjugated to the polypeptide and (ii) hydroxyethylmethacrylate.

A $13^{th}$ aspect is a composition the $11^{th}$ aspect, wherein the molar ratio of the methacrylic acid conjugated to the polypeptide and the hydroxyethylmethacrylate is between 1 to 15 and 1 to 5.

A $14^{th}$ aspect is a composition of the $11^{th}$ aspect, wherein the molar ratio of the methacrylic acid conjugated to the polypeptide and the hydroxyethylmethacrylate is about 1 to 9.

A $15^{th}$ aspect is a composition of any of aspects 4-13, wherein the polymer is formed from polymerization of hydroxyethlymethacrylate and MAA-$PEO_4$-polypeptide, wherein MMA is methacrylic acid, and PEO is polyethylene oxide.

A $16^{th}$ aspect is a composition of any of aspects 4-15, wherein the weight percentage of the polypeptide relative to the polymer conjugated to the polypeptide is greater than 10%.

A $17^{th}$ aspect is a composition of any of aspects 4-15, wherein the weight percentage of the polypeptide relative to the polymer conjugated to the polypeptide is greater than 40%.

A $18^{th}$ aspect is a composition of any of aspects 4-17, wherein the polypeptide is a cell adhesive polypeptide.

A $19^{th}$ aspect is a composition of any of aspects 4-18, wherein the polypeptide comprises an RGD sequence.

An $20^{th}$ aspect is a composition of any of aspects 4-19, wherein the polypeptide is a selected from the group of a vitronectin polypeptide, a collagen polypeptide, of a laminin polypeptide, a bone sialoprotein polypeptide, and a fibronectin polypeptide.

A $21^{st}$ aspect is a composition of any of aspects 4-20, wherein the polypeptide is a vitronectin polypeptide.

A $22^{nd}$ aspect is a composition of any of aspects 4-21, wherein the polypeptide comprises an amino acid sequence of SEQ ID NO:27.

A $23^{rd}$ aspect is a composition of any of aspects 4-22, wherein the polymer conjugated to the polypeptide has a molecular weight of between 10 kilodaltons and 1000 kilodaltons.

A $24^{th}$ aspect is a composition of any of aspects 4-23, wherein the composition has a pH of between 7 and 8, and further comprises: glucose and one or more amino acids.

A $25^{th}$ aspect is a composition of any of aspects 4-24, further comprising cells.

A $26^{th}$ aspect is a composition of the $25^{th}$ aspect, wherein the cells are stem cells.

A $27^{th}$ aspect is a composition of the $25^{th}$ aspect, wherein the cells are human embryonic stem cells or human mesenchymal stem cells.

A $28^{th}$ aspect is a composition of any of aspects 4-27, wherein the composition is free of microcarriers.

A $29^{th}$ aspect is a composition of any of aspects 4-27, wherein the cell culture surface is the surface of a microcarrier, A $30^{th}$ aspect is a method for coating a surface of a cell culture article, comprising: (i) introducing a synthetic polymer having a covalently attached polypeptide to an aqueous cell culture medium to produce a polymer containing cell culture medium, wherein the synthetic polymer conjugated to a polypeptide is configured to attach to the surface of a cell culture article under cell culture conditions; (ii) disposing the polymer containing cell culture medium on the surface of the cell culture article to produce a coated article; and (iii) incubating the coated article in the medium under cell culture conditions to attach the synthetic polymer conjugated to the polypeptide to the surface of the cell culture article.

A 31$^{st}$ aspect is a method of the 30$^{th}$ aspect, wherein the cell culture medium composition is a chemically defined composition.

A 32$^{nd}$ aspect is a method of the 30$^{th}$ or 31$^{st}$ aspect, wherein the cell culture medium is free of animal derived components.

A 33$^{rd}$ aspect is a method for coating a surface of a cell culture article, comprising: (i) introducing a polymer having a covalently attached polypeptide to an aqueous cell culture medium to produce a polymer containing cell culture medium, wherein the polymer is selected from the group consisting of a polymer that has a linear backbone and is crosslink free, a polymer that has a branched backbone and that is crosslink free, and a star polymer that is crosslink free, wherein the polymer having the covalently attached polypeptide is soluble at 20° C. or less, wherein the aqueous solution is substantially free of organic solvents; (ii) disposing the polymer containing cell culture medium on the surface of the cell culture article to produce a coated article; and (iii) incubating the coated article in the medium under cell culture conditions to attach the polymer conjugated to the polypeptide to the surface of the cell culture article.

A 34$^{th}$ aspect is a method of the 33$^{rd}$ aspect, wherein the polymer has a linear backbone.

A 35$^{th}$ aspect is a method of the 31$^{st}$ or 32$^{nd}$ aspect, wherein the cell culture medium is free of animal derived components.

A 36$^{th}$ aspect is a method of any of aspects 33-35, wherein the cell culture medium composition is a chemically defined composition. A 37$^{th}$ aspect is a method of any of aspects 33-36, wherein incubating the coated article in the medium under cell culture conditions includes incubating the coated article in the medium at about 37° C.

A 38$^{th}$ aspect is a method of any of aspects 33-34, wherein a substantially similar polymer that it not conjugated to the polypeptide is insoluble in water at 25° C.

A 39$^{th}$ aspect is a method of any of aspects 33-38, wherein the weight percentage of the polypeptide relative to the polymer conjugated to the polypeptide is greater than 10%.

A 40$^{th}$ aspect is a method of any of aspects 33-38, wherein the weight percentage of the polypeptide relative to the polymer conjugated to the polypeptide is greater than 40%.

A 41$^{st}$ aspect is a method of any of aspects 33-40, wherein the polypeptide is a cell adhesive polypeptide.

A 42$^{nd}$ aspect is a method of any of aspects 33-41, wherein the polypeptide comprises an RGD sequence.

A 43$^{rd}$ aspect is a method of any of aspects 33-42, wherein the polypeptide is a selected from the group of a vitronectin polypeptide, a collagen polypeptide, of a laminin polypeptide, a bone sialoprotein polypeptide, and a fibronectin polypeptide.

A 44$^{th}$ aspect is a method of any of aspects 33-43, wherein the polypeptide is a vitronectin polypeptide.

A 45$^{th}$ aspect is a method of any of aspects 33-44, wherein the polypeptide comprises an amino acid sequence of SEQ ID NO:27.

A 46$^{th}$ aspect is a method of any of aspects 33-45, wherein the polymer is formed from at least one monomer comprising a conjugated polypeptide.

A 47$^{th}$ aspect is a method of the 46$^{th}$ aspect, wherein the at least one monomer comprising a conjugated polypeptide is methacrylic acid.

A 48$^{th}$ aspect is a method of the 46$^{th}$ aspect, wherein the polymer is formed from polymerization of (i) methacrylic acid conjugated to the polypeptide and (ii) hydroxyethylmethacrylate.

A 49$^{th}$ aspect is a method of any of aspects 33-45, wherein the polymer is formed from polymerization of a (i) monomer comprising a methacrylic acid functional group and (ii) hydroxyethmethacrylate.

A 50$^{th}$ aspect is a method of any of aspects 33-49, wherein the polymer conjugated to the polypeptide has a molecular weight of between 10 kilodaltons and 1000 kilodaltons.

A 51$^{st}$ aspect is a method of any of aspects 33-50, wherein the surface of the substrate has a water contact angle between 0° and 50°.

A 52$^{nd}$ aspect is a method of any of aspects 33-50, wherein the surface of the substrate has a water contact angle between 0° and 30°.

A 53$^{rd}$ aspect is a method of any of aspects 33-52, wherein the surface of the substrate is a plasma treated polystyrene surface.

A 54$^{th}$ aspect is a method for culturing cells, comprising: (i) introducing cells into a polymer-containing cell culture medium, wherein the polymer containing cell culture medium comprises a synthetic polymer having a covalently attached polypeptide, wherein the synthetic polymer conjugated to a polypeptide is configured to attach to the surface of a cell culture article under cell culture conditions; (ii) contacting the polymer containing cell culture medium and cells to a surface of a cell culture article to produce a coated article; and (iii) incubating the cells on the coated article in the medium under cell culture conditions, wherein incubating the coated article in the medium under cell culture conditions results in attachment of the synthetic polymer conjugated to the polypeptide to the surface of the cell culture article.

A 55$^{th}$ aspect is a method of the 54$^{th}$ aspect, wherein the cell culture medium is free of animal derived components.

A 56$^{th}$ aspect is a method of the 54$^{th}$ or 55$^{th}$ aspect, wherein the cell culture medium composition is a chemically defined composition.

A 57$^{th}$ aspect is a method for culturing cells, comprising: (i) introducing cells into a polymer-containing cell culture medium, wherein the polymer containing cell culture medium comprises a polymer having a covalently attached polypeptide, wherein the polymer is selected from the group consisting of a polymer that has a linear backbone and is crosslink free, a polymer that has a branched backbone and is crosslink free, and a star polymer that is crosslink free, wherein the polymer having the covalently attached polypeptide is soluble in water at 20° C. or less, wherein the aqueous solution is substantially free of organic solvents; (ii) contacting the polymer containing cell culture medium and cells to a surface of a cell culture article to produce a coated article; and (iii) incubating the cells on the coated article in the medium under cell culture conditions, wherein incubating the coated article in the medium under cell culture conditions results in attachment of the polymer conjugated to the polypeptide to the surface of the cell culture article.

A 58$^{th}$ aspect is a method of the 57th aspect, wherein the polymer has a linear backbone.

A 59th aspect is a method of the 57th or 58th aspect, wherein the cell culture medium is free of animal derived components.

A 60th aspect is a method of any of aspects 57-59, wherein the cell culture medium composition is a chemically defined composition.

A 61st aspect is a method of any of aspects 57-60, wherein incubating the coated article in the medium under cell culture conditions includes incubating the coated article in the medium at about 37° C.

A 62nd aspect is a method of any of aspects 57-61, wherein a substantially similar polymer that it not conjugated to the polypeptide is insoluble in water at 25° C.

A 63rd aspect is a method of any of aspects 57-62, wherein the weight percentage of the polypeptide relative to the polymer conjugated to the polypeptide is greater than 40%.

A 64th aspect is a method of any of aspects 57-63, wherein the weight percentage of the polypeptide relative to the polymer conjugated to the polypeptide is greater than 60%.

A 65th aspect is a method of any of aspects 57-64, wherein the polypeptide is a cell adhesive polypeptide.

A 66th aspect is a method of any of aspects 57-65, wherein the polypeptide comprises an RGD sequence.

A 67th aspect is a method of any of aspects 57-66, wherein the polypeptide is a selected from the group of a vitronectin polypeptide, a collagen polypeptide, of a laminin polypeptide, a bone sialoprotein polypeptide, and a fibronectin polypeptide.

A 68th aspect is a method of any of aspects 57-67, wherein the polypeptide is a vitronectin polypeptide.

A 69th aspect is a method of any of aspects 57-69, wherein the polypeptide comprises an amino acid sequence of SEQ ID NO:27.

A 70th aspect is a method of any of aspects 57-69, wherein the polymer is formed from at least one monomer comprising a conjugated polypeptide.

A 71st aspect is a method of the 70th aspect, wherein the at least one monomer comprising a conjugated polypeptide is methacrylic acid.

A 72nd aspect is a method of the 70th aspect, wherein the polymer is formed from polymerization of (i) methacrylic acid conjugated to the polypeptide and (ii) hydroxyethylmethacrylate.

A 73rd aspect is a method of any of aspects 57-69, wherein the polymer is formed from polymerization of a (i) monomer comprising a methacrylic acid functional group and (ii) hydroxyethmethacrylate.

A 74th aspect is a method of any of aspects 59-73, wherein the polymer conjugated to the polypeptide has a molecular weight of between 10 kilodaltons and 1000 kilodaltons.

A 75th aspect is a method of any of aspects 57-74, wherein the surface of the substrate has a water contact angle between 0° and 50°.

A 76th aspect is a method of any of aspects 57-75, wherein the surface of the substrate has a water contact angle between 0° and 30°.

A 77th aspect is a method of any of aspects 57-76, wherein the surface of the substrate is a plasma treated polystyrene surface.

A 78th aspect is a method of any of aspects 57-77, wherein the cells are stem cells.

A 79th aspect is a method of the 78th aspect, wherein the cells are human embryonic stem cells or human mesenchymal stem cells.

Non-limiting examples of compositions, methods, and articles described herein are presented below for purposes of example.

EXAMPLES

Example 1: Culture on Pre-Coated Substrate Vs. Polymer in Medium

Cells were cultured in 6-well plates that were either pre-coated with MesenCult-XF Attachment Substrate ("MC-ASB") (StemCell Technologies, Cat. No. 05424), poly (HEMA-co-MAA-PEO4-VN) ("polyHEMA-co-VN"), or uncoated Corning CellBIND® plates (Corning Cat. No. 3335) or Costar® TC-treated plates (Corning Cat. No. 3516). PolyHEMA-co-VN was prepared as described as follows. Briefly, peptide monomer MAA-PEG4-VN (methacrylic acid-[polyethylene glycol]$_4$-vitronectin, where vitronectin has an amino acid sequence of SEQ ID NO:27) was purchased from American Peptide Company Inc. who synthesized the molecule using a solid peptide synthesizer. This monomer was copolymerized using 1:9 molar ratio with hydroxyethyl methacrylate (HEMA) in ethanol using thermal free radical polymerization and obtained the final polyHEMA-co-VN peptide copolymer.

For uncoated plates, MC-ASB or polyHEMA-co-VN was added to the cell culture medium and plated along with cells. Cell culture medium was MesenCult-XF complete medium ("MC-XF") Basal Medium (StemCell Technologies, Cat. No. 054020), which included MesenCult-XF Basal Medium (StemCell Technologies, Cat. No. 05421), MesenCult-XF Supplement (5×) (StemCell Technologies, Cat. No. 05422) and 2 mM L-Glutamine (Stem Cell Technologies, Cat. No. 07100).

A. Preparation of Pre-Coated Vessels i. MesenCult Attachment Substrate

MC-ASB was pre-coated following the manufacturer's instructions. Briefly, MC-ASB was dissolved in water at a concentration of 1 mg/ml as a stock solution. For coating, the MC-ASB stock solution was further diluted 1:28 in sterile PBS without Ca++ or Mg++(Life Technologies cat no. 14190) and 0.8 ml was added per well to a TCT plate. The plate was stored in a covered Nalgene container overnight at 4° C. for protein adsorption. Before cell culture, the plate was allowed to warm to room temperature for 20-30 minutes and washed with sterile cell culture water down the edge of well. The water was swirled around to rinse the entire surface and then aspirated off.

ii. polyHEMA-co-VN

Gamma sterilized polyHEMA-co-VN powder was reconstituted aseptically to a concentration of 2 mg/ml in sterile tissue culture water to generate a stock solution. The stock solution was gently rocked back and forth and allowed to dissolve for 5 minutes at room temperature. In a CELL-Bind® 6-well plate, 25 µl of polymer stock solution was diluted into 1 ml of sterile water in each well and incubated at 37° C. for 1 hour. The plate was washed with sterile cell culture water down the edge of each well of the plate. The water was swirled around to rinse the entire surface and then aspirated off.

iii. Matrigel

Matrigel® was diluted 1:30 and coated on TCT 6-well plates as a control surface for hESC seeding and subsequent culture.

B. Cell Culture i. hMSCs

Bone-marrow derived stem cells donor #2637, p4 cells were propagated on MC-ASB pre-coated surface in MC-XF. Cells were passaged when the cells reached 80% confluency. Cells were briefly rinsed with dPBS (Life Technologies, cat no. 14190) and then incubated with MesenCult-ACF Enzymatic Dissociation solution (StemCell Tech cat, no. 05427) for about 2 minutes. The cells were gently tapped from the surface, pipetted up and down a few times and then transferred to a 15 ml centrifuge tube. The flask was then rinsed with MesenCult-ACF Enzyme Inhibition solution (StemCell Tech, cat no. 05428) and then added to the tube containing the cells. The cells were spun down at 1200-1500 RPM for 6 minutes. Cell counts and viability were obtained from a Vi-Cell, automated cell viability analyzer (Beckman-Coulter). The pre-coated MC-ASB plate, CellBIND and pre-coated polyHEMA-co-VN plate were seeded with hMSC cells in MC-XF at a cell density of 3500 cells/cm$^2$. For uncoated plates, cell suspension was further supplemented with 0.05 mg/ml, 0.025 mg/ml, 0.012 mg/ml and 0.006 mg/ml of polyHEMA-co-VN or 0.037 mg/ml and 0.0074 mg/ml of MC-ASB using corresponding stock solution. 4 ml of cell mixture suspension with or without attachment supplement was added to each well. The medium was changed every 2-3 days during the cultures.

a. Cell Count and Staining

Cells cultured under each condition were harvested from 4 to 5 wells of the 6-well plate and pooled together and transferred into a 15 ml centrifuge tube containing 1 ml of Fetal Bovine Serum (Life Technologies, Cat no, 16000). All wells were then rinsed with dPBS and added to the cell suspension in the 15 ml tube. Cells were spun down at 1200-1500 RPM for 5-6 minutes and then resuspended in 3-5 mls of MC-XF. Cell count and viablity were obtained from Vi-Cell. To show the uniformity of the cell coverage, one well on each plate was crystal violet stain solution.

ii. hESCs

Human ESC-BGO1v was purchased from Life Technology and was used for testing in control or experimental conditions. Chemically defined medium mTeSR1 was purchased from Stem Cell Technology and used as standard medium for all hESC culture experiments reported here. Matrigel® was purchased from BD Sciences. CellBind and TCT 6-well plates were purchased from Corning Life Sciences.

PolyHEMA-co-VN was added in mTeSR1 at concentration of 0.006 mg/ml to 0.025 mg/ml and mixed with BGO1v cells for seeding in CellBind 6-well plates.

Cells were seeded at $0.8 \times 10^6$ per well and feed everyday after 2 days. No polymer was supplemented in medium during re-feeding. Cell morphology was observed using optical microscopy every day. Cell count and viability were obtained from Vi-Cell after 4 days.

C. Results and Discussion i. hMSCs

Figure 5A:
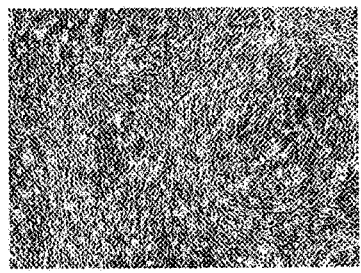
FIGS. 5a-c are images of human mesenechymal stem cells (hMSCs) cultured on different surfaces in chemically defined medium with our without attachment supplement.
Figure 5B:
Figure 5C:
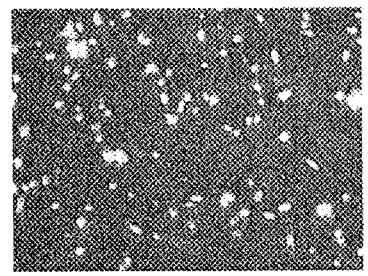
Figure 6A:
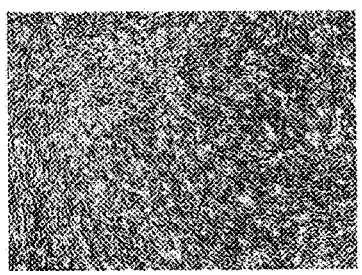
FIGS. 6a-f are images of hMSCs cultured on different surfaces in chemically defined medium with or without attachment supplement.
Figure 6B:
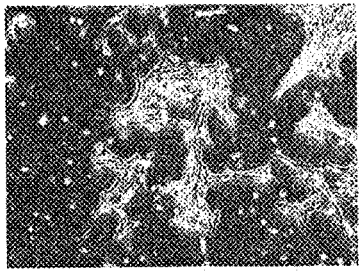
Figure 6C:
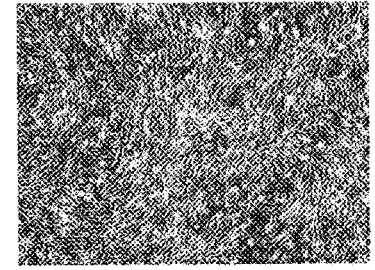
Figure 6D:
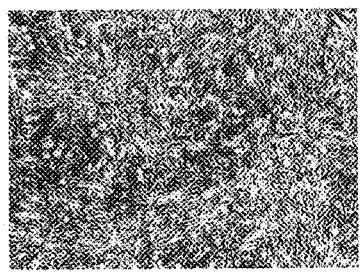
Figure 6E:
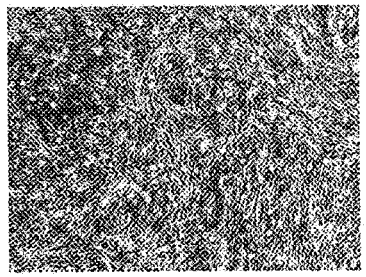
Figure 6F:
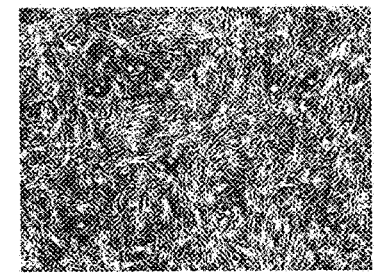

FIG. 5 presents images of cells cultured on wells of 6-well TCT plate, where the wells were FIG. 5a pre-coated with MC-ASB, FIG. 5b uncoated, but the seeding cell culture medium contained 0.037 mg/ml MC-ASB, and FIG. 5c uncoated, but the seeding cell culture medium contained 0.0074 mg/ml MC-ASB. As shown, pre-coated MC-ASB supported normal attachment and proliferation of hMSC (FIG. 5a). In contrast, addition of MC-ASB to cell culture medium and plating onto uncoated surfaces did not provide similar attachment support for hMSCs at the tested concentrations of 0.037 mg/ml (FIG. 5b) or 0.0074 mg/ml (FIG. 5c).

We selected 0.037 mg/ml and 0.0074 mg/ml MC-ASB concentrations because, 0.037 mg/ml was the concentration of MC-ASB solution used to pre-coat MC-ASB, which provided successful cell performance, and 0.0074 mg/ml provided the same amount of material in each well in the pre-coated wells. Due to 4 ml higher volume of medium used in cell culture vs. 0.8 ml used in pre-coating process, 5× dilution was applied.

In contrast to MC-ASB, polyHEMA-co-VN supplemented in medium effectively supported growth of hMSC. This growth was comparable to the surface pre-coated with polyHEMA-co-VN. Without polyHEMA-co-VN, the medium alone failed to do so. With reference to FIG. 6 images of hMSCs cultured on CellBind® surfaces with and without polyHEMA-co-VN are shown. Cells cultured on pre-coated polyHEMA-co-VN (FIG. 6a), uncoated CellBind® without polyHEMA-co-VN added to seeding cell culture medium (FIG. 6b), uncoated CellBind® with 0.006 mg/ml polyHEMA-co-VN added to seeding cell culture medium (FIG. 6c), uncoated CellBind® with 0.012 mg/ml polyHEMA-co-VN added to seeding cell culture medium (FIG. 6d), uncoated CellBind® with 0.025 mg/ml polyHEMA-co-VN added to seeding cell culture medium (FIG. 6e), and uncoated CellBind® with 0.050 mg/ml polyHEMA-co-VN added to seeding cell culture medium (FIG. 6f) are shown.

Referring now to FIG. 7, images of crystal violet-stained hMSCs cultured in different surfaces are shown. The images are of hMSCs cultured on FIG. 7a TCT surface pre-coated with MC-ASB; FIG. 7b non-pre-coated TCT surface with seeding medium supplemented with 0.037 mg/ml of MC-ASB; FIG. 7c non-pre-coated TCT surface with seeding medium supplemented with 0.0074 mg/ml of MC-ASB; FIG. 7d polyHEMA-co-VN pre-coated CellBind® surface; FIG. 7e non-pre-coated CellBind® surface; FIG. 7f non-pre-coated CellBind® surface with seeding medium supplemented with 0.006 mg/ml polyHEMA-co-VN; FIG. 7g non-pre-coated CellBind® surface with seeding medium supplemented with 0.012 mg/ml polyHEMA-co-VN; FIG. 7h non-pre-coated CellBind® surface with seeding medium supplemented with 0.025 mg/ml polyHEMA-co-VN; FIG. 7i non-pre-coated CellBind® surface with seeding medium supplemented with 0.050 mg/ml polyHEMA-co-VN.

Figure 7A:
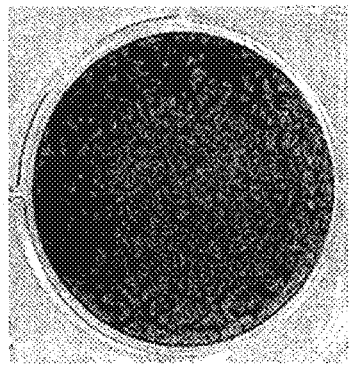
FIGS. 7a-i are images of crystal violet stained hMSCs cultured on different surfaces in chemically defined medium with or without attachment supplement.
Figure 7B:
Figure 7C:
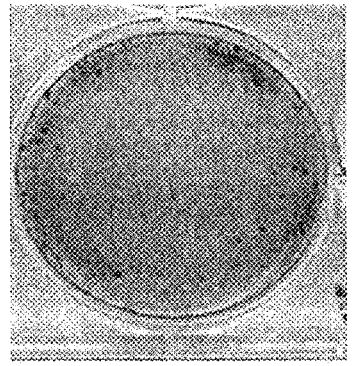
Figure 7D:
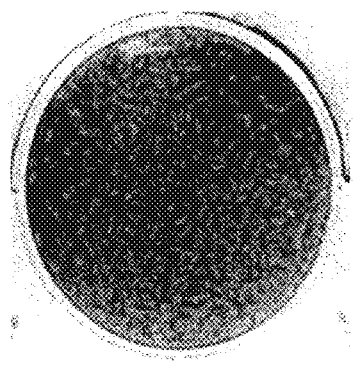
Figure 7E:
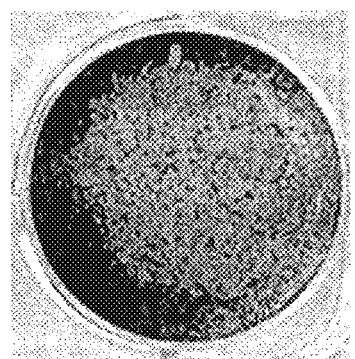
Figure 7F:
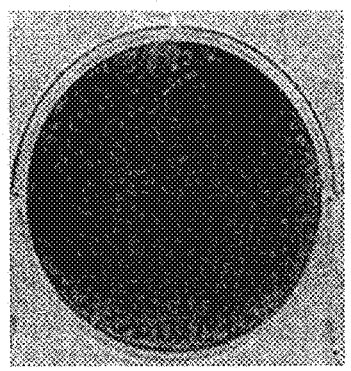
Figure 7G:
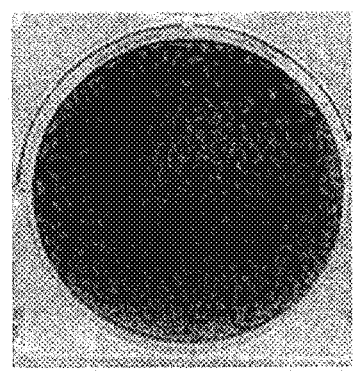
Figure 7H:
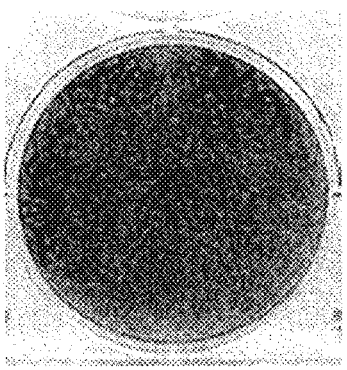
Figure 7I:
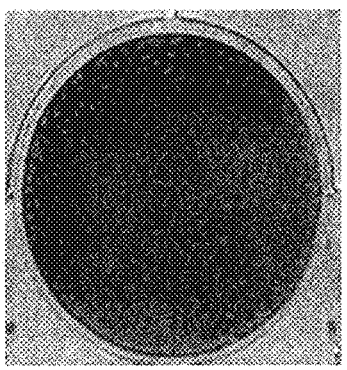

As shown in FIG. 7, pre-coated MC-ASB plates FIG. 7a support hMSC attachment, but not non-precoated plates where the seeding culture medium was supplemented with MC-ASB did not support attachment FIGS. 7b-c. In contrast, both pre-coated polyHEMA-co-VN plates FIG. 7d and non-pre-coated polyHEMA-co-VN plates where the seeding cell culture medium was supplemented with polyHEMA-co-VN FIGS. 7f-g supported hMSC attachment. Uncoated CellBind® plates in which polyHEMA-co-VN was not added to the seeding medium did not perform well for hMSC attachment FIG. 7e.

Figure 8:
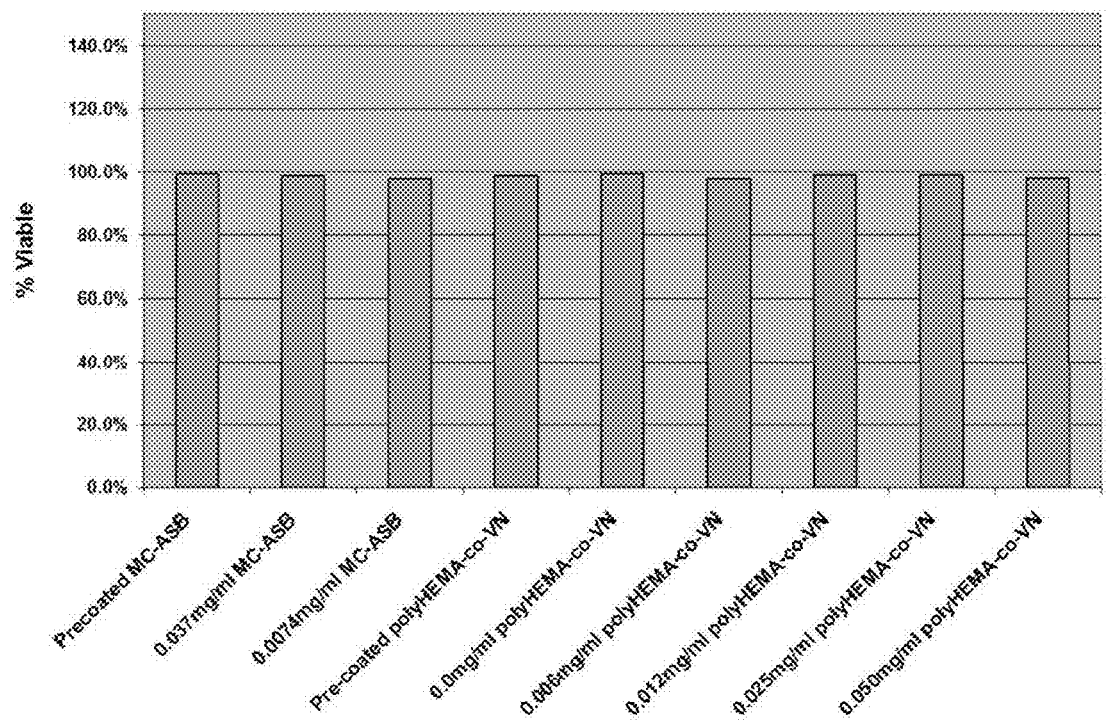
FIG. 8 is a bar graph showing the percentage of viable hMSCs cultured on various surfaces in chemically defined medium.

Referring now to FIG. 8, a graph showing the percentage of viable cells observed each of the polyHEMA-co-VN and MC-ASB surfaces is shown. While the number of cells attached to the various surfaces varied, the viability of those that did attach was near 100% for all surfaces tested.

Figure 9:
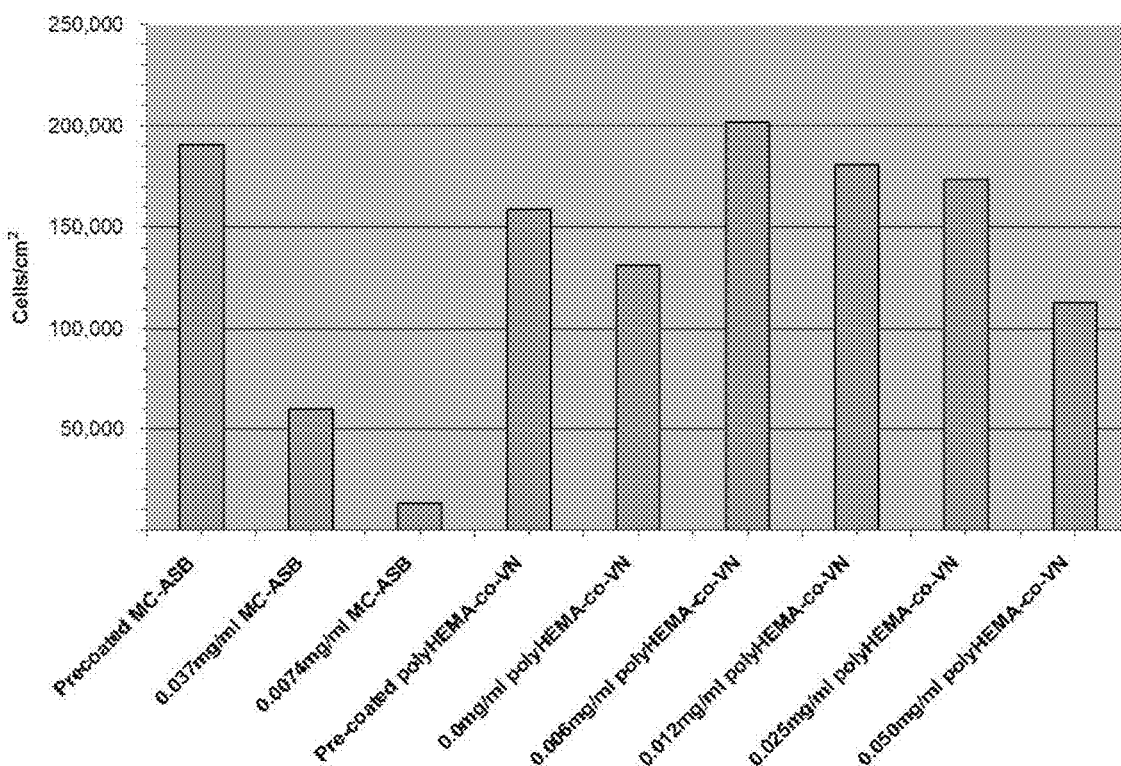
FIG. 9 is a bar graph showing the cell density (cells/cm$^2$) of hMSCs cultured on various substrates in chemically defined medium.

Referring now to FIG. 9, a graph showing the number of cell that attached to each of the polyHEMA-co-VN and MC-ASB surfaces is shown. These results confirm the results shown above and discussed with regard to FIG. 7. That is, pre-coated MC-ASB supported attachment and growth, while un-pre-coated wells where MC-ASB was added to the seeding culture medium did not support attachment. In contrast, both un-pre-coated wells where polyHEMA-co-VN was added to the seeding medium and pre-coated polyHEMA-co-VN surfaces supported attachment of hMSCs.

These results suggest that polyHEMA-co-VN, but not MC-ASB, can efficiently be adsorbed to the substrate surface from medium and quickly provides for hMSCs attachment and growth. With increase of polymer concentration of polyHEMA-co-VN, the cell numbers decreased without effecting cell morphology and surface coverage. Extra polymer left over in the solution after absorption may reduce the cell attachment but the impact was minimal. This suggests that this polymer has little side-effect to hMSC in medium and is safe for the cell culture.

In conclusion, polyHEMA-co-VN can be used as medium supplement to enable hMSC attachment and growth directly on traditional cell culture substrates. This polymer may provide a new way to make synthetic chemically defined media for cell therapeutic applications.

ii. hESCs

As with hMSCs, the addition of polyHEMA-co-VN to seeding cell culture medium supported hESC attachment and growth on non-pre-coated surfaces.

Figure 10A:
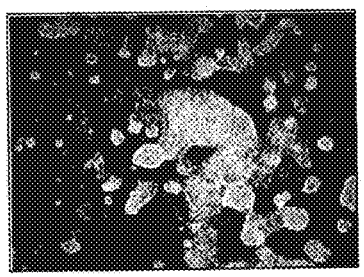
FIGS. 10a-c are images of human embryonic stem cells (hESCs) cultured on various surfaces for two days in chemically defined medium with or without attachment supplement.
Figure 10B:
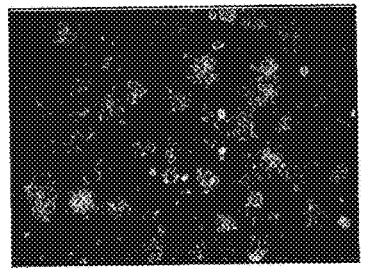
Figure 10C:
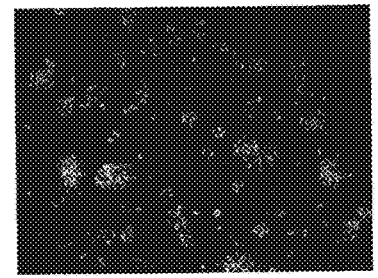

Referring now to FIG. 10, images of hESCs at day 2 are shown on Matrigel® coated TCT plates FIG. 10c and on un-pre-coated CellBind® plates in which the cell seeding medium was supplemented with 0.006 mg/ml polyHEMA-co-VN FIG. 10b or 0.25 mg/ml polyHEMA-co-VN FIG. 10a are shown. As shown, the hESC attached and spread very well in 0.006 mg/ml concentration polyHEMA-co-VN which was comparable to Matrigel surface as shown in FIG. 10b and FIG. 10c. When the seeding medium was supplemented with 0.025 mg/ml, more clusters of the cells was observed, which suggests more interaction between cells as shown in FIG. 10a.

Figure 11A:
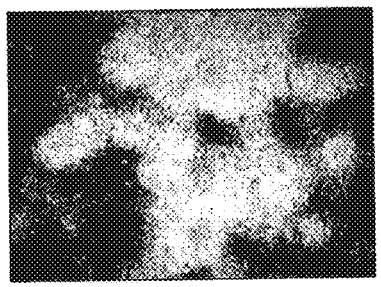
FIGS. 11a-c are images of hESCs cultured on various surfaces for four days in chemically defined medium with or without attachment supplement.
Figure 11B:
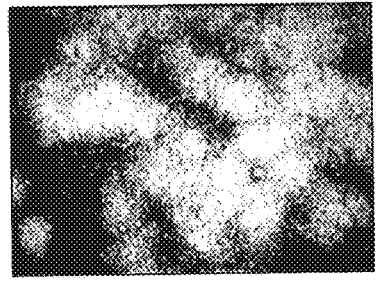
Figure 11C:
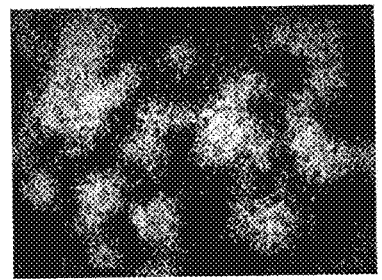

Referring now to FIG. 11, images of hESCs at day 4 are shown on Matrigel® coated TCT plates FIG. 11c and on un-pre-coated CellBind® plates in which the cell seeding medium was supplemented with 0.006 mg/ml polyHEMA-co-VN FIG. 11b or 0.25 mg/ml polyHEMA-co-VN FIG. 11a are shown. When the lower concentration polyHEMA-co-VN was used to supplement the seeding medium, the cells continued to maintain good morphology comparable to the Matrigel® coated surface as shown in FIG. 11b and FIG. 11c. Continued attachment and growth was also observed with the higher concentration polyHEMA-co-VN (FIG. 11a).

Figure 12:
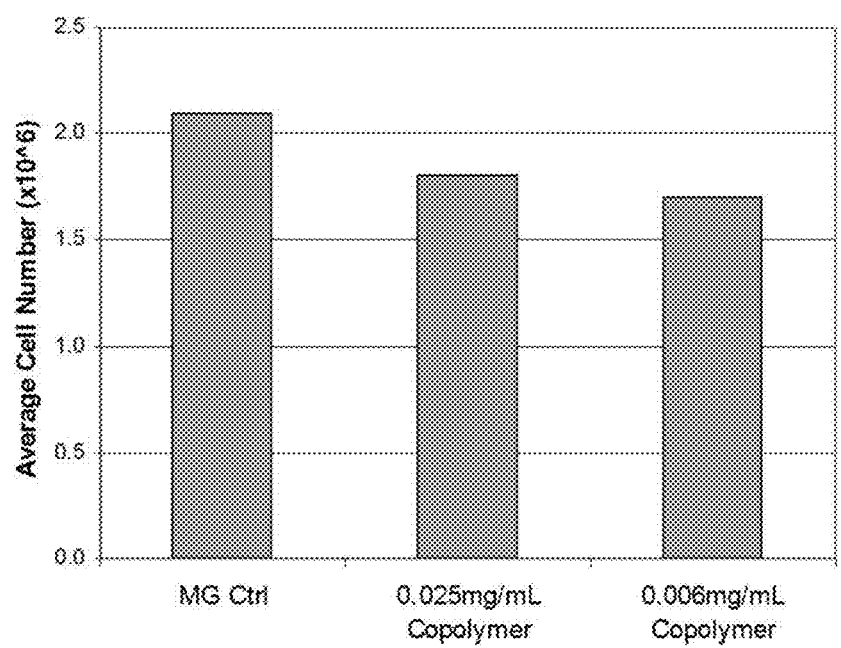
FIG. 12 is a bar graph showing average cell number of hESCs cultured on various surfaces.

Referring now to FIG. 12, a graph of cell number after four days of culture on Matrigel®, un-pre-coated surfaces where the seeding medium was supplement with 0.025 mg/ml polyHEMA-co-VN, and un-pre-coated surfaces where the seeding medium was supplement with 0.0.006 mg/ml polyHEMA-co-VN are shown. As shown in FIG. 12, the final cell number is comparable between Matrigel control and supplemented polyHEMA-co-VN.

Overall, the higher concentration polyHEMA-co-VN resulted in more cell clustering and a more cystic morphology. However, the cell number was not affected. These results suggested that concentration of the polymer in medium may affect how an added peptide polymer will interact with cells and cells clusters.

Thus, embodiments of SYNTHETIC ATTACHMENT MEDIUM FOR CELL CULTURE are disclosed. One skilled in the art will appreciate that the compositions, coatings, articles, methods, etc. described herein can be practiced with embodiments other than those disclosed. The disclosed embodiments are presented for purposes of illustration and not limitation.

What is claimed is:

1. An aqueous cell culture medium composition comprising:
   glucose, at least one amino acid and a synthetic copolymer having a covalently attached polypeptide;
   wherein the synthetic copolymer is formed from copolymerization of (i) methacrylic acid conjugated to the polypeptide and (ii) hydroxyethylmethacrylate;
   wherein when the aqueous cell culture medium containing the synthetic copolymer is introduced into a cell culture article, the synthetic copolymer attaches to the surface of the cell culture article under cell culture conditions.

2. The aqueous cell culture medium composition of claim 1, wherein the cell culture medium composition is a chemically defined composition.

3. The aqueous cell culture medium composition of claim 1 wherein synthetic copolymer is introduced to cell culture medium in a dry state.

4. The aqueous cell culture medium composition of claim 1 wherein the synthetic copolymer is added to cell culture media dissolved in water.

5. The aqueous cell culture medium composition of claim 1, wherein the molar ratio of the methacrylic acid conjugated to the polypeptide and the hydroxyethylmethacrylate is between 1 to 50 and 1 to 1.

6. The aqueous cell culture medium composition of claim 1 wherein the synthetic copolymer is formed from copolymerization of the hydroxyethylmethacrylate and MAA-PEO4-polypeptide, wherein MAA is the methacrylic acid, and PEO is polyethylene oxide.

7. The aqueous cell culture medium composition of claim 1, wherein the weight percentage of the polypeptide relative to the copolymer conjugated to the polypeptide is greater than 10%.

8. The aqueous cell culture medium composition of claim 1, wherein the polypeptide is a cell adhesive polypeptide.

9. The aqueous cell culture medium composition of claim 1, wherein the polypeptide comprises an RGD sequence.

10. The aqueous cell culture medium composition of claim 1, wherein the polypeptide is a vitronectin polypeptide.

11. The aqueous cell culture medium composition of claim 1, wherein the polypeptide comprises an amino acid sequence of SEQ ID NO:27.

12. The aqueous cell culture medium composition of claim 1, wherein the copolymer conjugated to the polypeptide has a molecular weight of between 10 kilodaltons and 1000 kilodaltons.

13. The aqueous cell culture medium composition of claim 1 wherein the copolymer has a linear backbone and is crosslink free, wherein the copolymer having the covalently attached polypeptide is soluble in water at 20° C. or less, and wherein the aqueous solution is substantially free of organic solvents.

14. The aqueous cell culture medium composition of claim 1, wherein the surface of the cell culture article is formed from a ceramic, glass, plastic, polymer, copolymer, or combination thereof.

15. The aqueous cell culture medium composition of claim 14, wherein the surface of the cell culture article is formed from soda-lime glass, pyrex glass, vycor glass, quartz glass, silicon, poly(vinyl chloride), poly(vinyl alcohol), poly(methyl methacrylate), poly(vinyl acetate-co-maleic anhydride), poly(dimethylsiloxane) monomethacrylate, cyclic olefin polymers, fluorocarbon polymers, polysytrenes, polypropylene, polyethyleneimine, poly(styrene-co-maleic anhydride), or poly(ethylene-co-acrylic acid).

16. The aqueous cell culture medium composition of claim 14, wherein the cell culture article is chosen from multi-well plates, jars, petri dishes, flasks, beakers, glass bead microcarriers, polymer bead microcarriers, roller bottles, slides, tubes, cover slips, membranes, hollow fibers, cups, spinner bottles, perfusion chambers, bioreactors, and fermenters.

17. The aqueous cell culture medium composition of claim 16, wherein the cell culture article is chosen from multi-well plates, petri dishes, flasks, and beakers.

* * * * *

UNITED STATES PATENT AND TRADEMARK OFFICE
CERTIFICATE OF CORRECTION

PATENT NO. : 11,046,931 B2  
APPLICATION NO. : 16/371252  
DATED : June 29, 2021  
INVENTOR(S) : Stephen Joseph Caracci et al.

Page 1 of 1

It is certified that error appears in the above-identified patent and that said Letters Patent is hereby corrected as shown below:

On the Title Page

In Column 1, item (73), Assignee, Line 1, delete "Coming" and insert -- Corning --, therefor.

In Column 2, item (56), Other Publications, Line 18, delete "selenocystine" and insert -- selenocysteine --, therefor.

In Column 2, item (56), Other Publications, Line 28, delete "(2006." and insert -- (2006). --, therefor.

On page 2, in Column 1, item (56), Other Publications, Line 1, delete "Melkorunian" and insert -- Melkoumian --, therefor.

On page 2, in Column 1, item (56), Other Publications, Line 6, delete "(2010." and insert -- (2010). --, therefor.

On page 2, in Column 1, item (56), Other Publications, Line 10, delete "huan" and insert -- human --, therefor.

On page 2, in Column 2, item (56), Other Publications, Line 12, delete "(3-40," and insert -- (3-4), --, therefor.

On page 2, in Column 2, item (56), Other Publications, Line 12, delete "(2010." and insert -- (2010). --, therefor.

In the Claims

In Column 42, Lines 39-40, Claim 15, delete "polysytrenes," and insert -- polystyrenes, --, therefor.

Signed and Sealed this  
Seventh Day of September, 2021

Drew Hirshfeld  
*Performing the Functions and Duties of the*  
*Under Secretary of Commerce for Intellectual Property and*  
*Director of the United States Patent and Trademark Office*